US009422259B2

(12) United States Patent
Nelson et al.

(10) Patent No.: US 9,422,259 B2
(45) Date of Patent: Aug. 23, 2016

(54) SYNTHETIC TRANSTAGANOLIDE AND BASILIOLIDE PRODUCTS, DERIVATIVES THEREOF, AND SYNTHESIS METHODS THEREOF

(71) Applicant: California Institute of Technology, Pasadena, CA (US)

(72) Inventors: Hosea Nelson, San Francisco, CA (US); Kei Murakami, Kyoto (JP); Scott C. Virgil, Pasadena, CA (US); Brian M. Stoltz, San Marino, CA (US); Jonathan R. Gordon, Beverly Hills, CA (US)

(73) Assignee: California Institute of Technology, Pasadena, CA (US)

(*) Notice: Subject to any disclaimer, the term of this patent is extended or adjusted under 35 U.S.C. 154(b) by 0 days.

(21) Appl. No.: 14/529,911

(22) Filed: Oct. 31, 2014

(65) Prior Publication Data

US 2015/0051411 A1 Feb. 19, 2015

Related U.S. Application Data

(62) Division of application No. 13/929,425, filed on Jun. 27, 2013, now Pat. No. 8,912,347, which is a division of application No. 13/353,314, filed on Jan. 18, 2012, now abandoned.

(60) Provisional application No. 61/433,844, filed on Jan. 18, 2011.

(51) Int. Cl.
*C07D 313/06* (2006.01)
*C07D 311/00* (2006.01)
*C07D 493/08* (2006.01)
*C07D 493/18* (2006.01)
*C07D 493/16* (2006.01)

(52) U.S. Cl.
CPC ............ *C07D 311/00* (2013.01); *C07D 493/08* (2013.01); *C07D 493/16* (2013.01); *C07D 493/18* (2013.01)

(58) Field of Classification Search
CPC .................................................. C07D 311/00
USPC ....................................................... 549/268
See application file for complete search history.

(56) References Cited

U.S. PATENT DOCUMENTS 8,912,347 B2 12/2014 Nelson et al.
2012/0184754 A1 7/2012 Nelson et al.
2015/0051411 A1* 2/2015 Nelson ................ C07D 493/08 549/281

OTHER PUBLICATIONS

Nelson et al. Organic Letters, 2008, 10(1), 25-8.*
Protective Groups in Organic Chemistry, McCombie, 1973 Protection of carboxylic acid, pp. 183-215 p. 210, lines 7-10.*
E. J. Corey et al., J. Am. Chem. Soc. 1972, 94, 6190-6191.*
Larsson, Organic Letters (2009), 11(3), 657-660.*
Rubal, Phytochemistry (Elsevier) (2007), 68(19), 2480-2486.*
Crisp, G.T.; Glink, P. T. Tetrahedron, 1994, 50, 2623.*
Corey, E. J. et aL, "Protection of Hydroxyl Groups as tert-Butyldimethylsilyl Derivatives", Communications to the Editor, Journal of the American Chemical Society, Aug. 23, 1972, vol. 94, No. 17, pp. 6190-6191.
Dai, Chaoyang et al., "The First General Method for Palladium-Catalyzed Negishi Cross-Coupling of Aryl and Vinyl Chlorides: Use of Commercially Available Pd(P(t-Bu)3)2 as a Catalyst," J. Am. Chem. Soc. 2001, 123, pp. 2719-2724.
Dorwald, F.A., "Side Reactions in Organic Synthesis," 2005, Wiley-VCH, Weinheim, p. IX of Preface p. 1-15.
Kozytska Mariya V. et al., "On the intramolecular pyrone Dieis-Alder approach to basiliolide B", Tetrahedron Letters, 2008, 49, pp. 2899-2901.
Kozytska, Mariya V. et al., "Synthetic approach toward basiliolide B", Abstracts of Papers, 234th National Meeting of the American Chemical Society, Boston, MA, Aug. 19-23, 2007; American Chemical Society; Washington, DC, 2007; ORGN 1012, 1 pg.
Kozytska, Mariya V. et al., Abstracts of Papers, 58th Southeast Regional Meeting of the American Chemical Society, Augusta, GA, Nov. 1-4, 2006; American Chemical Society; Washington, DC, 2006; SRM06 011 (On Order).
Kozytska, Mariya V., "I. Siletanylmethyllithium, An Ambiphilic Siletane li. Synthetic Approach to Basiliolide B", PhD Thesis, Florida State University College of Arts and Sciences: Aug. 19, 2008, 297 pp.
Larsson, Rikard et al.; "Biomimetic Synthesis toward the Transtaganolides/Basiliolides"; Organic Letters; 2009; vol. 11; No. 3; pp. 657-660.
Liang, Yun et aL "Cy2NH•HX-Promoted Cyclizations of o-(Alk-1-ynyl)benzoates and (Z)-Alk-2-en-4-ynoate with Copper Halides to Synthesize Isocoumarins and α-Pyrone", Synthesis, 2007, No. 3, pp. 400-406.
Loffler, Achim et al., "Alkoxyacetylenes from Alkyl 1,2-Dichlorovinyl Ethers," Synthesis, May 1992, vol. 5, pp. 495-498.
MaWhinney, Thomas P. et al., "*N*-Methyl-*N*-(*tert*-butyldimethylsily l) trifluoroacetamide and Related N-*tert*-Butyldimethylsilyl Amides as Protective Silyl Donors1", J. Org. Chem. 1982, 47, pp. 3336-3339.
Marshall, J. A., Organometallics in Synthesis: A Manual, (Ed.: M. Schlosser) John Wiley & Sons Ltd., West Sussex, 2002, pp. 457 (On Order).
Mason, M. R. et al., "Fluoride-Induced Reduction of Palladium(II) and Platinum(II) Phosphine Complexes" Organometallics, 1992, 11, pp. 2212-2220.
Nelson, Hosea M. et al., "Progress toward the Synthesis of the Basiliolides and Transtaganolides: An Intramolecular Pyrone Diels-Alder Entry into a Novel Class of Natural Products", Organic Letters, 2008, vol. 10, No. 1, pp. 25-28.

(Continued)

*Primary Examiner* — Nizal Chandrakumar
(74) *Attorney, Agent, or Firm* — Foley Hoag LLP; David P. Halstead

(57) ABSTRACT

Compounds represented by Formula I are provided that include synthetic transtaganolide and basiliolide products. Derivatives of these compounds and methods of synthesis are also provided.

6 Claims, 17 Drawing Sheets

(56) References Cited

OTHER PUBLICATIONS

Nelson, et al., "A General Approach to the Basiliolide/Transtaganolide Natural Products: Total Syntheses of Basiliolide B, epi-8-Basiliolide B, Transtaganolide C, and Transtaganolide D", Angew. Chem. Int. Ed., vol. 50, pp. 3688-3691 (2011).

Nelson, Hosea M. et al., "Progress toward the synthesis of the transtaganolide/basiliolide natural products: an Ireland-Claisen approach", Tetrahedron Letters, 2009, 50, pp. 1699-1701.

Raucher, Stanley et al., "A Convenient Procedure for the Preparation of Ethoxyacetylene and Ethoxyethynyl Carbinols", J. Org. Chem., 1987, 52, pp. 2332-2333.

Rubal, Juan J. et al., "A pyran-2-one and four meroterpenoids from Thapsia transtagana and their implication in the biosynthesis of transtaganolides", Phytochemistry, 2007, 68, pp. 2480-2486.

Sakamoto, Takao et al., "Palladium-Catalyzed Cross-Coupling Reaction of Ethoxy(tributylstannyl)acetylene with Aryl Iodides," Letters, Synlett, 1992, No. 6, p. 502.

Sakamoto, Takao et al., "Synthesis of Ethoxyethynylarenes by the Palladium-Catalyzed Reaction of Aryl Iodides with Ethoxy(trialkylstannyl)acetylenes1)", Chem. Pharm. Bull, 1994, vol. 42, No. 10, pp. 2032-2035.

Saouf, Abderrahmane et al., "Transtaganolides A-D: Novel Metabolites from Thapsia transtagana"; Organic Letters; 2005; vol. 7, No. 5; pp. 881-884.

Shibuya, Hirotaka et al., "Chemical Transfomation of Terpenoids. X.1) Ionophoretic Activities of Macrocyclic Lactone Epoxides Synthesized from Geraniol", Chem. Pharm. Bull., 1994, 42, pp. 293-299.

Venkatesh et al., "Role of the Development Scientist in Compound Lead Selection and Optimization," J. Pharm. Sci., 89(2):145-54 (2000) (p. 146, left column).

White, Craig, "Integration of supercritical fluid chromatography into drug discovery as a routine support tool Part I. Fast chiral screening and purification", Journal of Chromatography A, 1074, 2005, pp. 163-173.

Yao, Tuanli et al., "Synthesis of Isocoumarins and α-Pyrones via Electrophilic Cyclization", J. Org. Chem., 2003, 68, pp. 5936-5942.

Zhou, Xiongfei et al., "Base-Catalyzed Diels-Alder Reactions of 2H-Pyran-2,5-diones: A Mild Approach to Basiliolide B", Organic Letters, 2008, vol. 10, No. 24, pp. 5525-5528.

International Search Report and Written Opinion for corresponding International Patent Application No. PCT/US2012/021785; mailed Aug. 28, 2012: 8pp.

\* cited by examiner

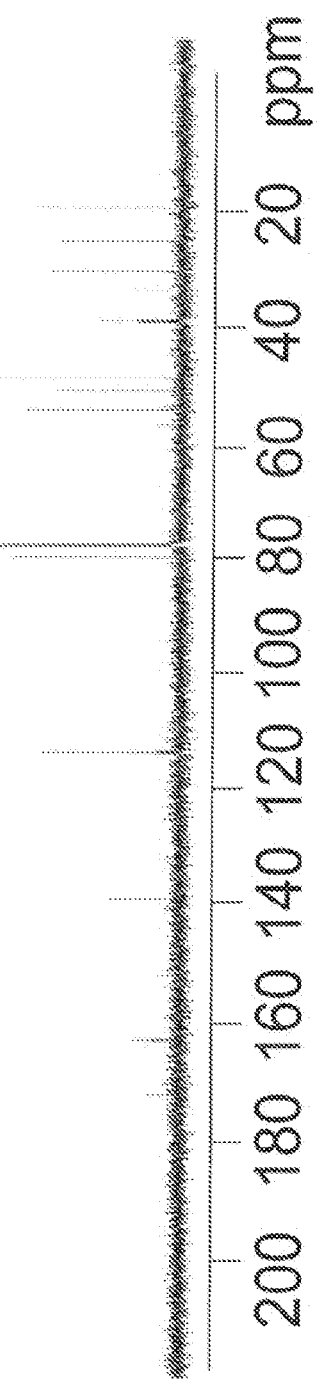
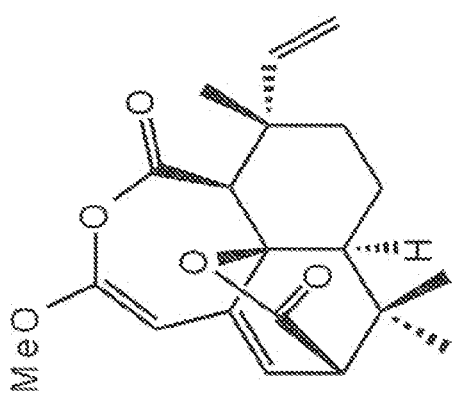
FIG. 2
Transtaganolide C

FIG. 6
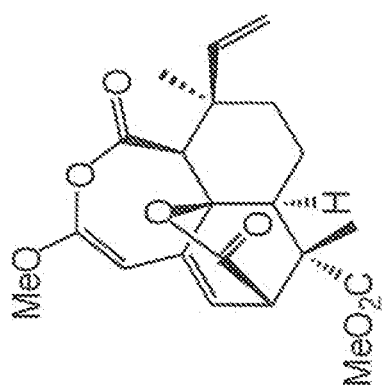
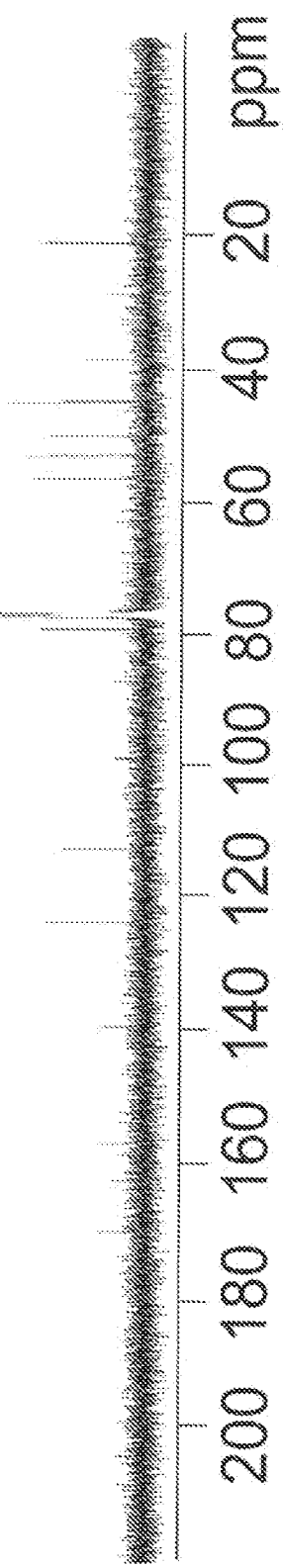

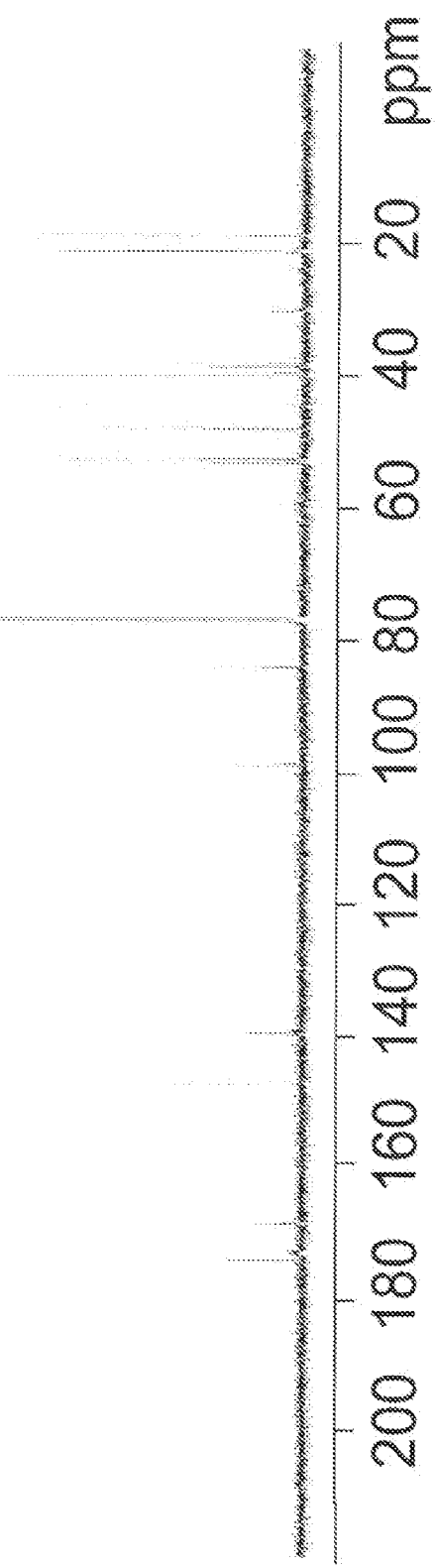
FIG. 11
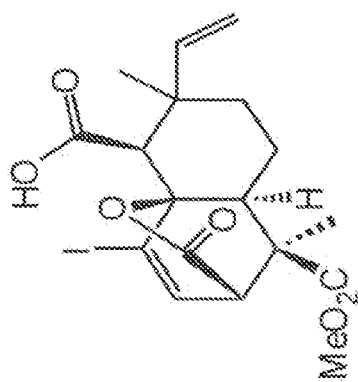

FIG. 14
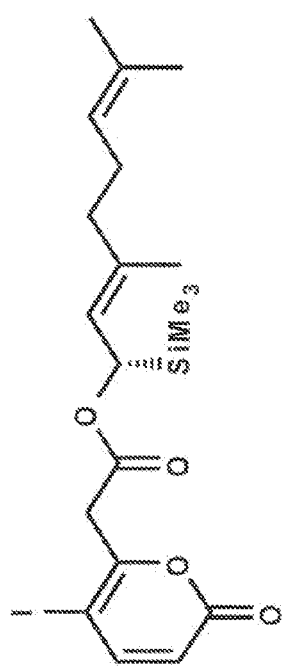
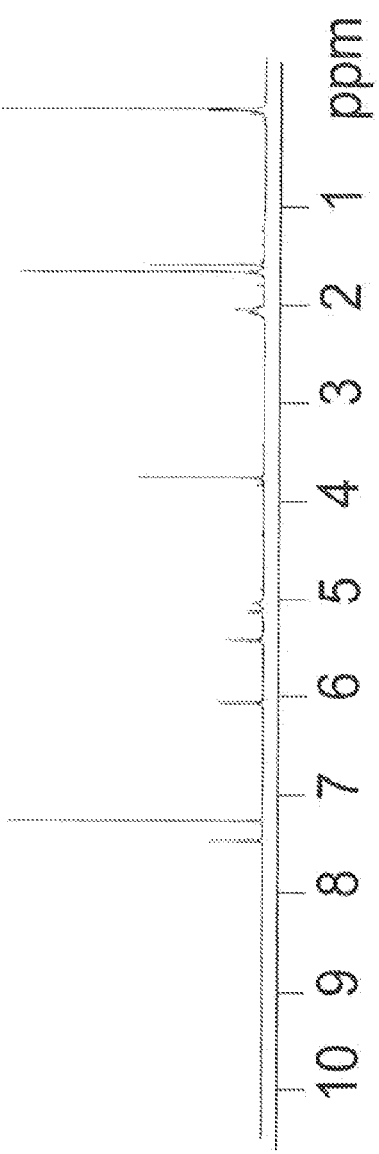

FIG. 15
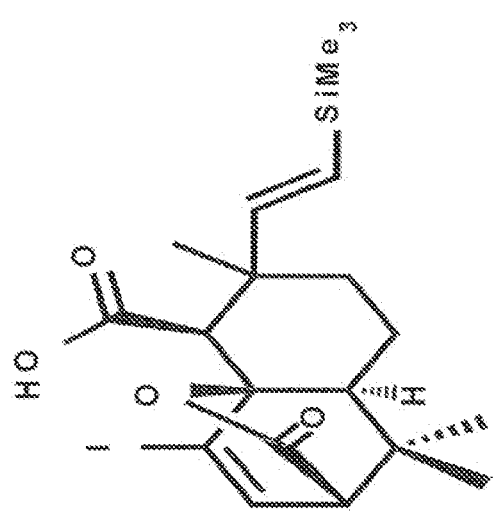
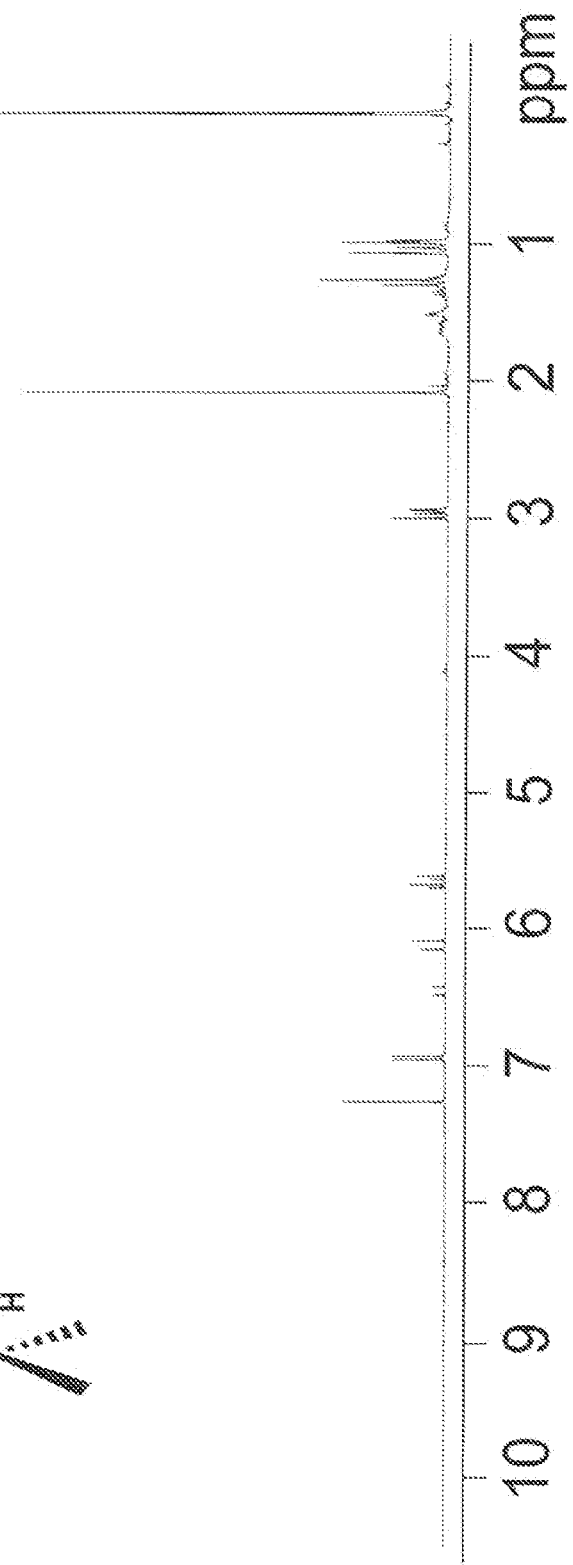

SYNTHETIC TRANSTAGANOLIDE AND BASILIOLIDE PRODUCTS, DERIVATIVES THEREOF, AND SYNTHESIS METHODS THEREOF

CROSS-REFERENCE TO RELATED APPLICATION(S)

The present application is a divisional of U.S. application Ser. No. 13/929,425, filed Jun. 27, 2013, pending, which is a divisional of U.S. applicaition Ser. No. 13/353,314 filed Jan. 18, 2012, which claims priority to and the benefit of U.S. Provisional Application Ser. No. 61/433,844, filed on Jan. 18, 2011, the entire contents of each of which are incorporated herein by reference.

BACKGROUND

The transtaganolides and basiliolides compounds 1-3 as shown in Diagram 1, are members of a growing family of natural products isolated from plants belonging to the genus *Thapsia*. Compounds within this group (e.g., compounds 1a, 1b, and 3a) have been shown to induce rapid mobilization of intracellular $Ca^{2+}$ stores. This activity has been attributed to the inhibition of calcium ATPases residing within the sarco/endoplasmic reticulum (SERCA-ATPases). *Thapsia* sp. are also the plan source of the commonly employed and structurally unrelated SERCA-ATPase inhibitor, thapsigargin (compound 4). Furthermore, Oikawa and coworkers have proposed a structure-function relationship to the widely utilized anti-malarial agent artemisinin (compound 5), which has also been proposed to act via ATPase inhibition. Other reports suggest a mode of action independent of ATPase inhibition.

Structurally, the transtaganolide/basiliolide molecules possess a dense array of functionalization and a polycyclic ring system comprised of trans-decalin framework, a bridging lactone (see 1a rings A and B) and an unprecedented cyclic acyl ketene acetal (ring C).

Diagram 1:

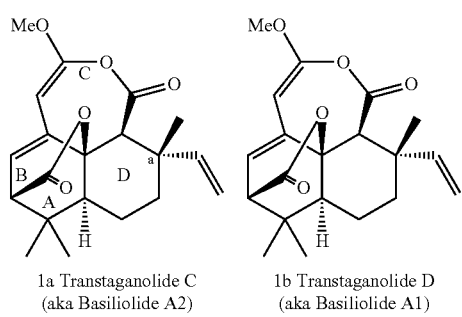

1a Transtaganolide C (aka Basiliolide A2)
1b Transtaganolide D (aka Basiliolide A1)

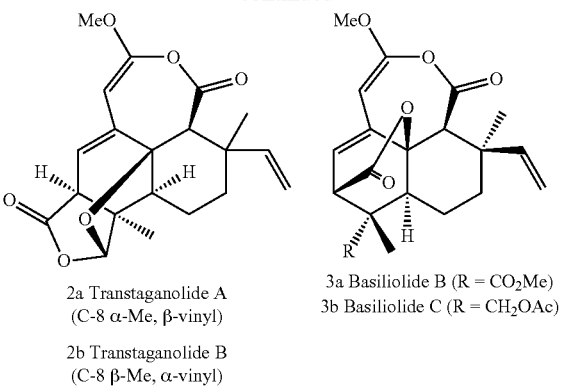

2a Transtaganolide A (C-8 α-Me, β-vinyl)
2b Transtaganolide B (C-8 β-Me, α-vinyl)
3a Basiliolide B (R = $CO_2Me$)
3b Basiliolide C (R = $CH_2OAc$)

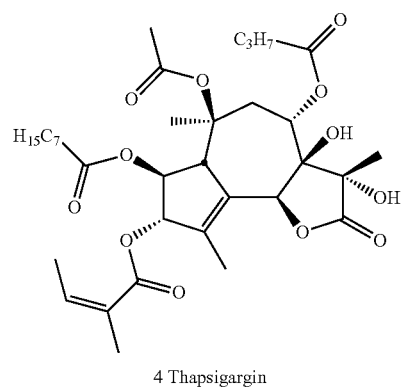

4 Thapsigargin

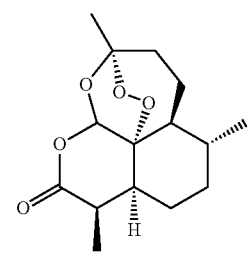

5 Artemisinin

Owing to the interesting biological activity and striking architectures, the transtaganolides (compounds 1 and 2) and basiliolides (compound 3) have inspired significant interest from the synthetic community. Despite these early developments by multiple research groups and the disclosure of these advanced intermediates, total synthesis of transtaganolides or basiliolides has not been reported.

SUMMARY

In some embodiments of the preset invention, a synthetic compound is provided represented by Formula I:

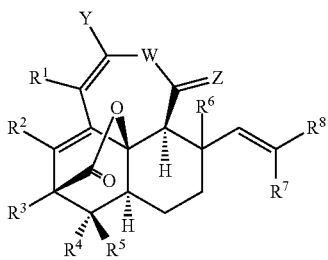

Formula I wherein:

Y is selected from —OR$^9$, —N, R$^{10}$, R$^{11}$, —SR$^{12}$, wherein R$^9$, R$^{10}$, R$^{11}$, and R$^{12}$ are each independently selected from hydrocarbyl, substituted hydrocarbyl, heteroatom-containing hydrocarbyl, or substituted heteroatom-containing hydrocarbyl;

W is selected from —O, —S, or —NR$^{21}$, wherein R$^{21}$ is hydrogen, hydrocarbyl, substituted hydrocarbyl, heteroatom-containing hydrocarbyl, or substituted heteroatom-containing hydrocarbyl;

Z is selected from —O, —S, or —NR$^{22}$, wherein R$^{22}$ is hydrogen, hydrocarbyl, substituted hydrocarbyl, heteroatom-containing hydrocarbyl, or substituted heteroatom-containing hydrocarbyl;

R$^1$, R$^2$, and R$^3$ are each independently selected from hydrogen, hydrocarbyl, substituted hydrocarbyl, heteroatom-containing hydrocarbyl, substituted heteroatom-containing hydrocarbyl;

R$^4$, R$^5$, and R$^6$ are independently selected from hydrogen, hydrocarbyl, substituted hydrocarbyl, heteroatom-containing hydrocarbyl, or substituted heteroatom-containing hydrocarbyl; and R$^7$ and R$^8$ are independently selected from hydrogen, hydrocarbyl, substituted hydrocarbyl, heteroatom-containing hydrocarbyl, or substituted heteroatom-containing hydrocarbyl; and any two or more adjacent R groups optionally combine to form a ring.

Some embodiments of the present invention are directed to a method of enriching for an enantiomer of Formula I, including synthesizing a compound of Formula III in which one of R$^{7'}$ and R$^{8'}$ is a silyl group and the other of R$^{7'}$ and R$^{8'}$ is hydrogen, including removing the silyl group to form an enantioselective compound; and reacting a compound of Formula II with the enantioselective Formula III compound, to form the compound of Formula I,

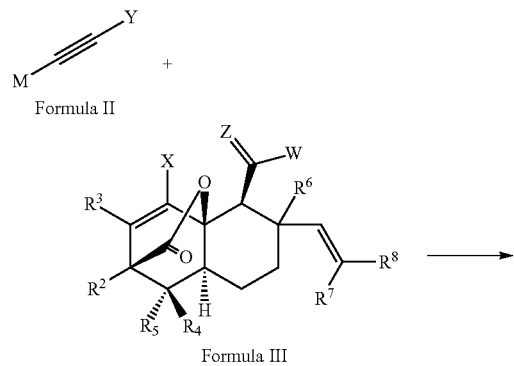

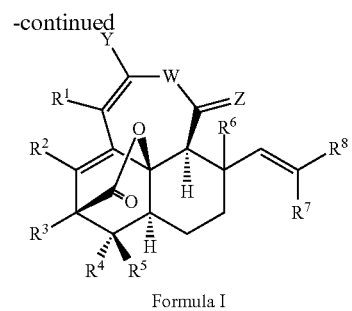

Formula I wherein:

Y is selected from —OR$^9$, —N, R$^{10}$, R$^{11}$, —SR$^{12}$, wherein R$^9$, R$^{10}$, R$^{11}$, and R$^{12}$ are each independently selected from hydrocarbyl, substituted hydrocarbyl, heteroatom-containing hydrocarbyl, or substituted heteroatom-containing hydrocarbyl;

M is selected from Li, Na, hydrogen, SiR$^{13}$R$^{14}$R$^{15}$, SnR$^{16}$R$^{17}$R$^{18}$, BR$^{19}$R$^{20}$, and ZnX$_2$ wherein R$^{13}$, R$^{14}$, R$^{15}$, R$^{16}$, R$^{17}$, and R$^{18}$ are each independently selected from hydrocarbyl or substituted hydrocarbyl, R$^{19}$ and R$^{20}$ are each independently selected from hydrocarbyl, substituted hydrocarbyl, heteroatom-containing hydrocarbyl, or substituted heteroatom-containing hydrocarbyl, and X is any halogen;

W is selected from —O, —S, or —NR$^{21}$, wherein R$^{21}$ is hydrogen, hydrocarbyl, substituted hydrocarbyl, heteroatom-containing hydrocarbyl, or substituted heteroatom-containing hydrocarbyl;

Z is selected from —O, —S, or —NR$^{22}$, wherein R$^{22}$ is hydrogen, hydrocarbyl, substituted hydrocarbyl, heteroatom-containing hydrocarbyl, or substituted heteroatom-containing hydrocarbyl;

R$^1$, R$^2$, and R$^3$ are each independently selected from hydrogen, hydrocarbyl, substituted hydrocarbyl, heteroatom-containing hydrocarbyl, or substituted heteroatom-containing hydrocarbyl; and R$^4$, R$^5$, and R$^6$ are each independently selected from hydrogen, hydrocarbyl, substituted hydrocarbyl, heteroatom-containing hydrocarbyl, or substituted heteroatom-containing hydrocarbyl; and any two or more adjacent R groups optionally combine to form a ring.

In other embodiments of the present invention, a compound, including a synthetic compound represented by Formula IV is provided:

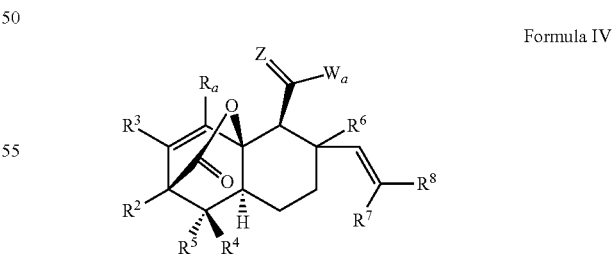

Formula IV wherein:

R$_a$ is selected from hydrocarbyl, substituted hydrocarbyl, heteroatom-containing hydrocarbyl, or substituted heteroatom-containing hydrocarbyl;

W$_a$ is selected from —OR$^x$, —SR$^{xx}$, and —NR$^{xxx}$R$^{xxxx}$, where each of R$^x$, R$^{xx}$, R$^{xxx}$ and R$^{xxxx}$ is independently selected from hydrogen, hydrocarbyl, substituted hydrocarbyl, heteroatom-containing hydrocarbyl, or substituted heteroatom-containing hydrocarbyl;

each of $R^3$ through $R^8$ is selected from hydrogen, hydrocarbyl, substituted hydrocarbyl, heteroatom-containing hydrocarbyl, or substituted heteroatom-containing hydrocarbyl;

Z is selected from —O, —S and —$NR^{22}$, wherein $R^{22}$ is selected from hydrocarbyl, substituted hydrocarbyl, heteroatom-containing hydrocarbyl, or substituted heteroatom-containing hydrocarbyl; and any two or more of $R_a$ and $R^3$ through $R^8$ optionally combine to form a ring.

In other embodiments of the present invention, a method of synthesizing a compound of Formula IV, includes reacting a compound of Formula IV-I with a compound of Formula IV-II according to reaction scheme 11 to form the compound of Formula IV:

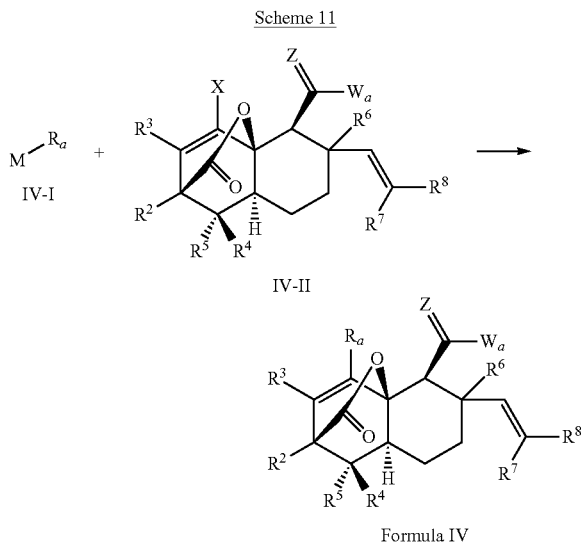

wherein:

$R_a$ is selected from hydrocarbyl, substituted hydrocarbyl, heteroatom-containing hydrocarbyl, or substituted heteroatom-containing hydrocarbyl;

$W_a$ is selected from —$OR^X$, —$SR^{XX}$, and —$NR^{XXX}R^{XXXX}$, where each of $R^X$, $R^{XX}$, $R^{XXX}$ and $R^{XXXX}$ is independently selected from hydrogen, hydrocarbyl, substituted hydrocarbyl, heteroatom-containing hydrocarbyl, or substituted heteroatom-containing hydrocarbyl;

each of $R^3$ through $R^8$ is selected from hydrogen, hydrocarbyl, substituted hydrocarbyl, heteroatom-containing hydrocarbyl, or substituted heteroatom-containing hydrocarbyl;

Z is selected from the group consisting of —O, —S and —$NR^{22}$, wherein $R^{22}$ is selected from hydrocarbyl, substituted hydrocarbyl, heteroatom-containing hydrocarbyl, or substituted heteroatom-containing hydrocarbyl;

M is selected from Li, Na, hydrogen, $SiR^{12}R^{14}R^{15}$, $SnR^{16}R^{17}R^{18}$, $BR^{19}R^{20}$, $MgX'_2$ and $ZnX''_2$, where:

each of $R^{13}$ through $R^{18}$ is independently selected from hydrocarbyl or substituted hydrocarbyl, each of $R^{19}$ and $R^{20}$ is independently selected from hydrogen, hydrocarbyl, substituted hydrocarbyl, heteroatom-containing hydrocarbyl, or substituted heteroatom-containing hydrocarbyl, and each of X' and X" is independently selected from halogens;

X is a halogen; and any two or more of $R_a$ and $R^3$ through $R^8$ optionally combined to form a ring.

BRIEF DESCRIPTION OF THE DRAWINGS

FIG. 2 is a $^{13}$C NMR spectrum of transtaganolide C (1a), according to aspects of the present invention.

FIG. 6 is a $^{13}$C NMR spectrum of basiliolide B (3a), according to aspects of the present invention.

FIG. 11 is a $^{13}$C NMR spectrum of iodoacid (6c), according to aspects of the present invention.

FIG. 14 is a $^1$H NMR spectrum of trimethylsilyl pyrone ester, according to aspects of the present invention.

FIG. 15 is a $^1$H NMR spectrum of trimethylsilyl iodoacid, according to aspects of the present invention.

DETAILED DESCRIPTION

Figure 1:
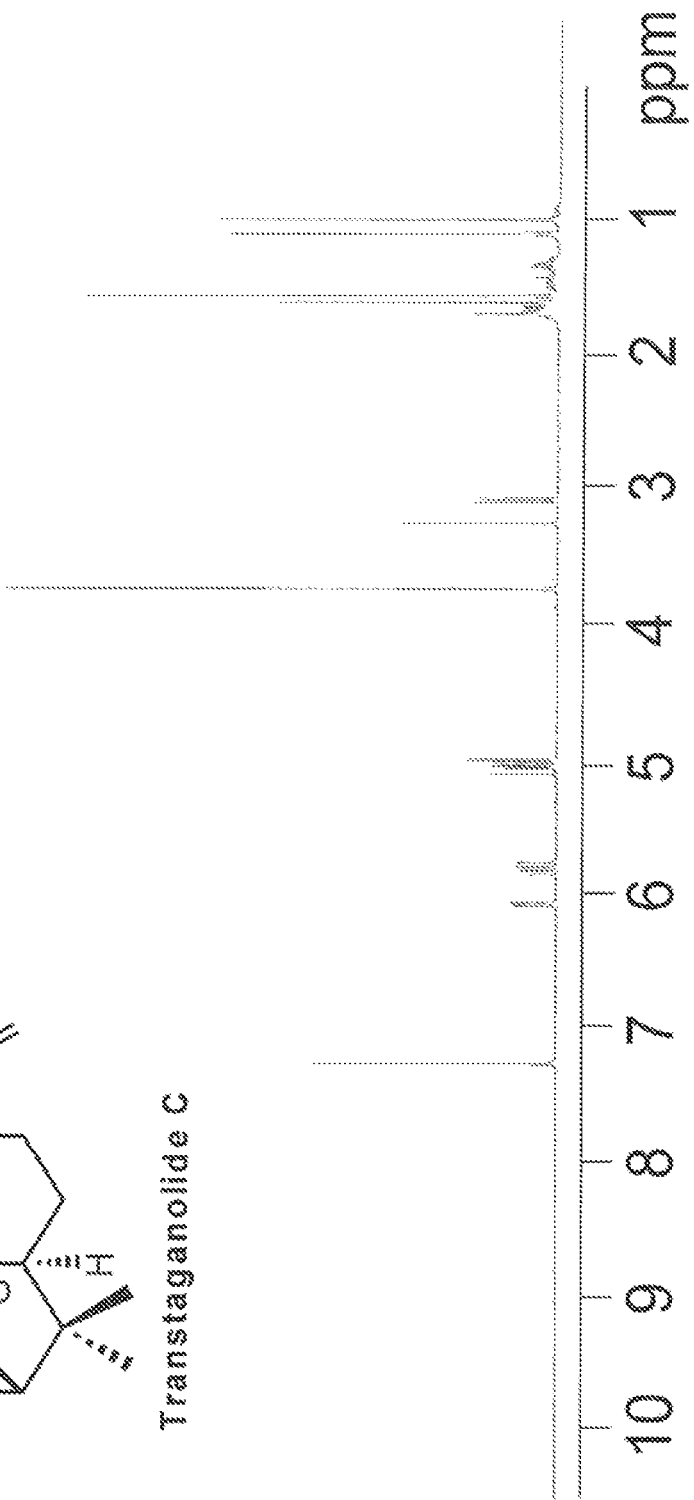
FIG. 1 is a $^1$H NMR spectrum of transtaganolide C (1a), according to aspects of the present invention.

It is to be understood that unless otherwise indicated this invention is not limited to specific reactants, reaction conditions, ligands, metal complexes, or the like, as such may vary. It is also to be understood that the terminology used herein is for the purpose of describing particular embodiments only and is not intended to be limiting.

Where lists are used to identify multiple embodiments, it is understood that modifiers stated at the beginning of the list apply to each element in the list. Thus, for example, in a list of "chiral compounds", each compound in the list is understood to be chiral.

As used in the specification and the appended claims, the singular forms "a," "an" and "the" include plural referents unless the context clearly dictates otherwise. Thus, for example, reference to "a compound" encompasses a combination or mixture of different compounds as well as a single compound, reference to "a functional group" includes a single functional group as well as two or more functional groups that may or may not be the same, and the like.

In this specification and in the claims that follow, reference will be made to a number of terms, which shall be defined to have the following meanings:

As used herein, the phrase "having the formula" or "having the structure" is not intended to be limiting and is used in the same way that the term "comprising" is commonly used.

The term "alkyl" as used herein refers to a linear, branched or cyclic saturated hydrocarbon group typically although not necessarily containing 1 to about 24 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl and the like. Generally, although again not necessarily, alkyl groups herein contain 1 to about 12 carbon atoms. The term "lower alkyl" intends an alkyl group of 1 to 6 carbon atoms, preferably 1 to 4 carbon atoms, and the specific term "cycloalkyl" intends a cyclic alkyl group, typically having 4 to 8, preferably 5 to 7, carbon atoms. The term "substituted alkyl" refers to alkyl substituted with one or more substituent groups, and the terms "heteroatom-containing alkyl" and "heteroalkyl" refer to alkyl in which at least one carbon atom is replaced with a heteroatom. If not otherwise indicated, the terms "alkyl" and "lower alkyl" include linear, branched, cyclic, unsubstituted, substituted, and/or heteroatom-containing alkyl and lower alkyl, respectively.

The term "alkenyl" as used herein refers to a linear, branched or cyclic hydrocarbon group of 2 to 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Preferred alkenyl groups herein contain 2 to 12 carbon atoms. The term "lower alkenyl" intends an alkenyl group of 2 to 6 carbon atoms, preferably 2 to 4 carbon atoms, and the specific term "cycloalkenyl" intends a cyclic alkenyl group, preferably having 5 to 8 carbon atoms. The term "substituted alkenyl" refers to alkenyl substituted with one or more substituent groups, and the terms "heteroatom-containing alkenyl" and "heteroalkenyl" refer to alkenyl in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkynyl" as used herein refers to a linear or branched hydrocarbon group of 2 to 24 carbon atoms containing at least one triple bond, such as ethynyl, n-propynyl, and the like. Preferred alkynyl groups herein contain 2 to 12 carbon atoms. The term "lower alkynyl" intends an alkynyl group of 2 to 6 carbon atoms, preferably 2 to 4 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The term "alkoxy" as used herein intends an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms, preferably 1 to 4 carbon atoms. Analogously, "alkenyloxy" and "lower alkenyloxy" respectively refer to an alkenyl and lower alkenyl group bound through a single, terminal ether linkage, and "alkynyloxy" and "lower alkynyloxy" respectively refer to an alkynyl and lower alkynyl group bound through a single, terminal ether linkage.

The term "aryl" as used herein, and unless otherwise specified, refers to an aromatic substituent containing a single aromatic ring or multiple aromatic rings that are fused together, directly linked, or indirectly linked (such that the different aromatic rings are bound to a common group such as a methylene or ethylene moiety). Preferred aryl groups contain 5 to 24 carbon atoms, and particularly preferred aryl groups contain 5 to 14 carbon atoms. Exemplary aryl groups contain one aromatic ring or two fused or linked aromatic rings, e.g., phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl substituent, in which at least one carbon atom is replaced with a heteroatom, as will be described in further detail infra.

The term "aryloxy" as used herein refers to an aryl group bound through a single, terminal ether linkage, wherein "aryl" is as defined above. An "aryloxy" group may be represented as —O-aryl where aryl is as defined above. Preferred aryloxy groups contain 5 to 24 carbon atoms, and particularly preferred aryloxy groups contain 5 to 14 carbon atoms. Examples of aryloxy groups include, without limitation, phenoxy, o-halo-phenoxy, m-halo-phenoxy, p-halo-phenoxy, o-methoxy-phenoxy, m-methoxy-phenoxy, p-methoxy-phenoxy, 2,4-dimethoxy-phenoxy, 3,4,5-trimethoxy-phenoxy, and the like.

The term "alkaryl" refers to an aryl group with an alkyl substituent, and the term "aralkyl" refers to an alkyl group with an aryl substituent, wherein "aryl" and "alkyl" are as defined above. Preferred alkaryl and aralkyl groups contain 6 to 24 carbon atoms, and particularly preferred alkaryl and aralkyl groups contain 6 to 16 carbon atoms. Alkaryl groups include, for example, p-methylphenyl, 2,4-dimethylphenyl, p-cyclohexylphenyl, 2,7-dimethylnaphthyl, 7-cyclooctylnaphthyl, 3-ethyl-cyclopenta-1,4-diene, and the like. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like. The terms "alkaryloxy" and "aralkyloxy" refer to substituents of the formula —OR wherein R is alkaryl or aralkyl, respectively, as just defined.

The term "acyl" refers to substituents having the formula —(CO)-alkyl, —(CO)-aryl, or —(CO)-aralkyl, and the term "acyloxy" refers to substituents having the formula —O(CO)-alkyl, —O(CO)-aryl, or —O(CO)-aralkyl, wherein "alkyl," "aryl", and "aralkyl" are as defined above.

The term "cyclic", "cycle", or "ring" refers to alicyclic or aromatic substituents that may or may not be substituted and/or heteroatom containing, and that may be monocyclic, bicyclic, or polycyclic. The term "alicyclic" is used in the conventional sense to refer to an aliphatic cyclic moiety, as opposed to an aromatic cyclic moiety, and may be monocyclic, bicyclic or polycyclic.

The terms "halo" and "halogen" are used in the convention sense to refer to a chloro, bromo, fluoro or iodo substituent.

"Hydrocarbyl" refers to univalent hydrocarbyl radicals containing 1 to about 30 carbon atoms, preferably 1 to about 24 carbon atoms, most preferably 1 to about 12 carbon atoms, including linear, branched, cyclic, saturated and unsaturated species, such as alkyl groups, alkenyl groups, aryl groups, and the like. The term "lower hydrocarbyl" intends a hydrocarbyl group of 1 to 6 carbon atoms, preferably 1 to 4 carbon atoms, and the term "hydrocarbylene" intends a divalent hydrocarbyl moiety containing 1 to about 30 carbon atoms, preferably 1 to about 23 carbon atoms, most preferably 1 to about 12 carbon atoms, including linear, branched, cyclic, saturated and unsaturated species. The term "lower hydrocarbylene" intends a hydrocarbylene group of 1 to 6 carbon atoms. "Substituted hydrocarbyl" refers to hydrocarbyl substituted with one or more substituent groups, and the terms "heteroatom-containing hydrocarbyl" and "heterohydrocarbyl" refer to hydrocarbyl in which at least one carbon atom is replaced with a heteroatom. Similarly, "substituted hydrocarbylene" refers to hydrocarbylene substituted with one or more substituent groups, and the terms "heteroatom-containing hydrocarbylene" and "heterohydrocarbylene" refer to hydrocarbylene in which at least one carbon atom is replaced with a heteroatom. Unless otherwise indicated, the term "hydrocarbyl" and "hydrocarbylene" are to be interpreted as including substituted and/or heteroatom-containing hydrocarbyl and hydrocarbylene moieties, respectively.

The term "heteroatom-containing" as in a "heteroatom-containing hydrocarbyl group" refers to a hydrocarbon molecule or a hydrocarbyl molecular fragment in which one or more carbon atoms is replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the term "heterocyclic" refers to a cyclic substituent that is heteroatom-containing, the terms "heteroaryl" and "heteroaromatic" respectively refer to "aryl" and "aromatic" substituents that are heteroatom-containing, and the like. It should be noted that a "heterocyclic" group or compound may or may not be aromatic, and further that "heterocycles" may be monocyclic, bicyclic, or polycyclic as described above with respect to the term "aryl."

By "substituted" as in "substituted alkyl," "substituted aryl," and the like, as alluded to in some of the aforementioned definitions, is meant that in the alkyl, aryl, or other moiety, at least one hydrogen atom bound to a carbon (or other) atom is replaced with one or more non-hydrogen substituents. Examples of such substituents include, without limitation: functional groups such as halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{24}$ aryloxy, acyl (including $C_2$-$C_{24}$ alkylcarbonyl (—CO-alkyl) and $C_6$-$C_{24}$ arylcarbonyl (—CO-aryl)), acyloxy (—O-acyl), $C_2$-$C_{24}$ alkoxycarbonyl (—(CO)—O-alkyl), $C_6$-$C_{24}$ aryloxycarbonyl (—(CO)—O-aryl), halocarbonyl (—CO)—X where X is halo), $C_2$-$C_{24}$ alkylcarbonato (—O—(CO)—O-alkyl), $C_6$-$C_{24}$ arylcarbonato (—O—(CO)—O-aryl), carboxy (—COOH), carboxylato (—COO$^-$), carbamoyl (—(CO)—NH$_2$), mono-($C_1$-$C_{24}$ alkyl)-substituted carbamoyl (—(CO)—NH($C_1$-$C_{24}$ alkyl)), di-($C_1$-$C_{24}$ alkyl)-substituted carbamoyl (—(CO)—N($C_1$-$C_{24}$ alkyl)$_2$), mono-($C_6$-$C_{24}$ aryl)-substituted carbamoyl (—(CO)—NH-aryl), di-($C_6$-$C_{24}$ aryl)-substituted carbamoyl (—(CO)—N (aryl)$_2$), d-N-($C_1$-$C_{24}$ alkyl), N-($C_6$-$C_{24}$ aryl)-substituted carbamoyl, thiocarbamoyl (—(CS)—NH$_2$), carbamido (—NH—(CO)—NH$_2$), cyano (—C≡N), isocyano (—N$^+$≡C$^-$), cyanato (—O—C≡N), isocyanato (—O—N$^+$≡C$^-$), isothiocyanato (—S—C≡N), azido (—N=N$^+$N=N$^-$), formyl (—(CO)—H), thioformyl (—(CS)—H), amino (—NH$_2$), mono-($C_1$-$C_{24}$ alkyl)-substituted amino, di-($C_1$-$C_{24}$ alkyl)-substituted amino, mono-($C_5$-$C_{24}$ aryl)-substituted amino, di-($C_5$-$C_{24}$ aryl)-substituted amino, $C_2$-$C_{24}$ alkylamido (—(CO)-alkyl), $C_6$-$C_{24}$ arylamido (—NH—(CO)-aryl), imino (—CR=NH where R=hydrogen, $C_1$-$C_{24}$ alkyl, $C_5$-$C_{24}$ aryl, $C_6$-$C_{24}$ alkaryl, $C_6$-$C_{24}$ aralkyl, etc.), alkylimino (—CR=N (alkyl), where R=hydrogen, $C_1$-$C_{24}$ alkyl, $C_5$-$C_{24}$ aryl, $C_6$-$C_{24}$ alkaryl, $C_6$-$C_{24}$ aralkyl, etc.), arylimino (—CR=N (aryl), where R=hydrogen, $C_1$-$C_1$-$C_{24}$ alkyl, $C_5$-$C_{24}$ aryl, $C_6$-$C_{24}$ alkaryl, $C_6$-$C_{24}$ aralkyl, etc.), nitro (—NO$_2$), nitroso (—NO), sulfo (—SO$_2$—OH), sulfonato (—SO$_2$—O$^-$), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{24}$ arylsulfinyl (—(SO)-aryl), $C_1$-$C_{24}$ alkylsulfonyl (—SO$_2$-alkyl), $C_5$-$C_{24}$ arylsulfonyl (—SO$_2$-aryl), boryl (—BH$_2$), borono (—B(OH)$_2$), boronato (—B (OR)$_2$ where R is alkyl or other hydrocarbyl), phosphono (—P(O)(OH)$_2$), phosphonato (—P(O)(O$^-$)$_2$), phosphinato (—P(O)(O$^-$)), phospho (—PO$_2$), and phosphino (—PH$_2$); and the hydrocarbyl moieties $C_1$-$C_{24}$ alkyl (preferably $C_1$-$C_{12}$ alkyl, more preferably $C_1$-$C_6$ alkyl), $C_2$-$C_{24}$ alkenyl (preferably $C_2$-$C_{13}$ alkenyl, more preferably $C_2$-$C_6$ alkenyl), $C_2$-$C_{24}$ alkynyl (preferably $C_2$-$C_{12}$ alkynyl, more preferably $C_2$-$C_6$ alkynyl), $C_5$-$C_{24}$ aryl (preferably $C_5$-$C_{14}$ aryl), $C_6$-$C_{24}$ alkaryl (preferably $C_6$-$C_{16}$ alkaryl), and $C_6$-$C_{24}$ aralkyl (preferably $C_6$-$C_{16}$ aralkyl).

In addition, the aforementioned functional groups may, if a particular group permits, be further substituted with one or more additional functional groups or with one or more hydrocarbyl moieties such as those specially enumerated above. Analogously, the above-mentioned hydrocarbyl moieties may be further substituted with one or more functional groups or additional hydrocarbyl moieties such as those specially enumerated.

When the term "substituted" appears prior to a list of possible substituted groups, it is intended that the term apply to every member of that group. For example, the phrase "substituted alkyl, alkenyl, and aryl" is to be interpreted as "substituted alkyl, substituted alkenyl, and substituted aryl." analogously, when the term "heteroatom-containing" appears prior to a list of possible heteroatom-containing groups, it is intended that the term apply to every member of that group. For example, the phrase "heteroatom-containing alkyl, alkenyl, and aryl" is to be interpreted as "heteroatom-containing alkyl, substituted alkenyl, and substituted aryl."

"Optional" or "optionally" means that the subsequently described circumstance may or may not occur, so that the description includes instances where the circumstance occurs and instances, where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

In the molecular structures herein, the use of bold and dashed lines to denote particular conformation of groups follows the IUPAC convention. A bond indicated by a broken line indicates that the group in question is below the general plane of the molecule as drawn (the "α" configuration), and a bond indicated by a bold line indicates that the group at the position in question is above the general plane of the molecule as drawn (the "β" configuration).

The terms "enantiomer excess," "enantiomeric excess," and "e.e." are used interchangeably and are defined as |F(+)−F(−)| for a mixture of (+)- and (−)-enantiomers, with composition given as the mole or weight fractions F(+) and F(−), such that F(+)+F(−)=1. When given as a percentage, enantiomer excess is defined by 100*|F(+)−F(−)|. "Enantioselective" is used to refer to a reactant that can enrich for one enantiomer. "Enantioenriched" refers the enriched product(s) having an increase of, or more of, one enantiomer compound.

The terms "racemate," "racemic form," and "racemic mixture" are used interchangeably to refer to a substantially equimolar mixture of two enantiomers, and can be designated using the (±) symbol.

A person of ordinary skill in the art recognizes that the temperature for a reaction can vary widely, producing the same reaction product, albeit at varying lengths of time. In general the compounds used herein are not stable above 120° C. Accordingly, all reactions disclosed herein for the disclosed compounds may be performed from 0 to 120° C. depending on the stability of the reagents (e.g. catalysts and solvents).

Initial efforts to synthesize basiliolides and transtaganolides utilized an intramolecular pyrone Diels-Alder cycloaddition to construct the oxabicyclo[2.2.2]octene moiety constituting the ABD ring system of compound 1 (transtaganolide C, D) and compound 3 (basiliolide B) as shown in Diagram 1, below (H. M. Nelson et. al, *Org. Lett.* 2008, 10, 25-28, M. V. Kozytska et al., *Tetrahedron Lett.* 2008, 49, 2899-2901; M. V. Kozytska et al., *Abstracts of Papers*, 234th National Meeting of the American Chemical Society, Boston, Mass., Aug. 19-23, 2007; American Chemical Society; Washington, D.C., 2007; ORGN 1012; M. V. Kozytska et al., *Abstracts of Papers*, 58th Southeast Regional Meeting of the American Chemical Society, Augusta, Ga., Nov. 1-4, 2006; American Chemical Society; Washington, D.C., 2006; SRM06 011; M. V. Kozytska, *I. Siletanylmethyllithium, an ambiphilic siletane II. Synthetic approach to basiliolide B*. PhD Thesis, Florida State University College of Arts and Sciences: 2008; and X. Zhou et al., *Org. Lett.* 2008, 10, 5525-5528, the entire contents of all of which are incorporated herein by reference.)

Diagram 1:

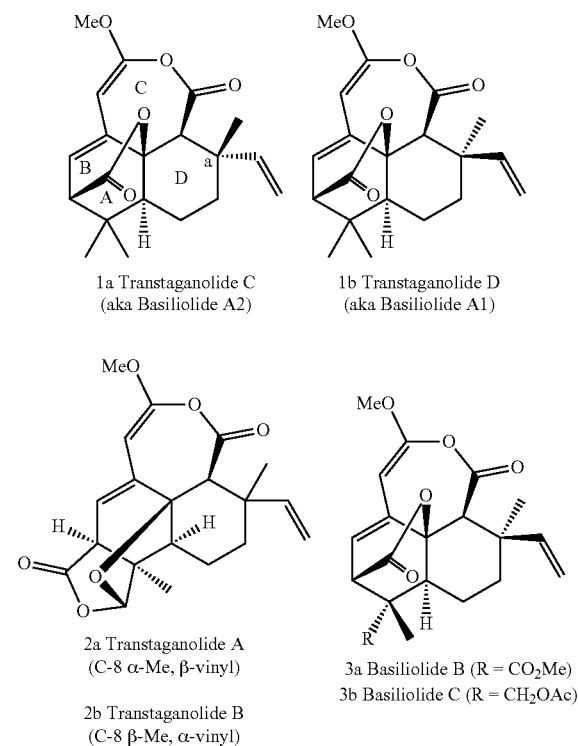

1a Transtaganolide C
(aka Basiliolide A2)

1b Transtaganolide D
(aka Basiliolide A1)

2a Transtaganolide A
(C-8 α-Me, β-vinyl)

2b Transtaganolide B
(C-8 β-Me, α-vinyl)

3a Basiliolide B (R = CO₂Me)
3b Basiliolide C (R = CH₂OAc)

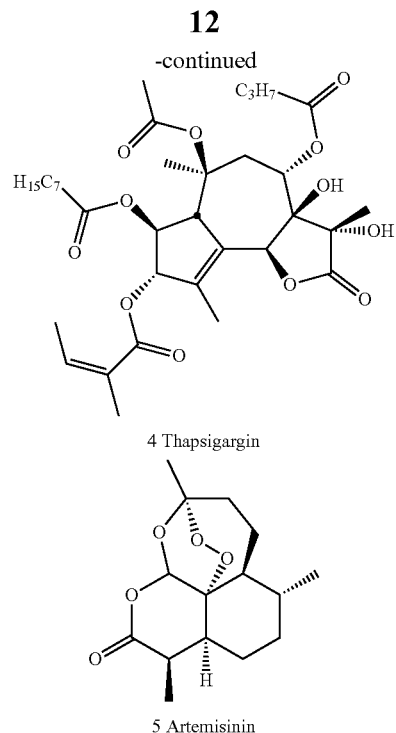

4 Thapsigargin

5 Artemisinin

Furthermore, H. M. Nelson, 2009, infra and R. Larsson et al., 2009, infra, have independently demonstrated a rapid and diastereoselective construction of the tricyclic core from a simple ester precursor via sequential Ireland-Claisen rearrangement/—intramolecular pyrone Diels-Alder cycloaddition (Scheme 1), as disclosed in H. M. Nelson et al., *Tetrahedron Lett.* 2009, 50, 1699-1701 and R. Larsson et al., *Org. Lett.* 2009, 11, 657-660, the entire contents of both of which are incorporated herein by reference. This Ireland-Claisen/Diels Alder two-step sequence shown in Scheme 1, smoothly installs the C(8) quaternary carbon as a 2:1 mixture of diastereomers with all other stereochemistry being controlled by the C(7) ester stereochemistry.

Scheme 1:

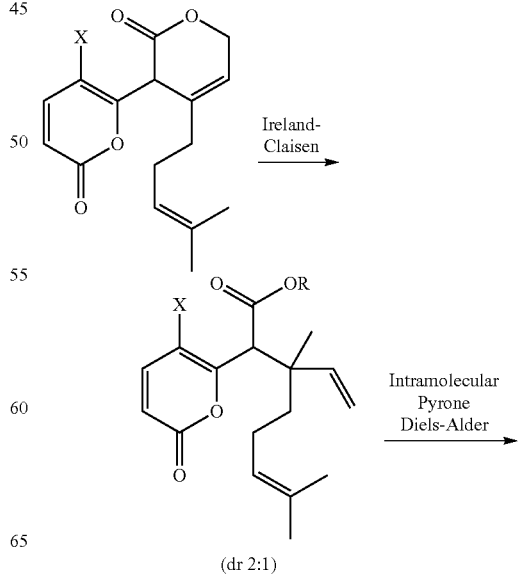

(dr 2:1)

-continued

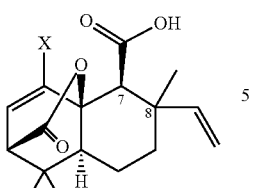

5

10

Despite these efforts, complete synthesis of a basiliolide or transtaganolide compound has not yet been reported.

The challenge in advancing intermediates akin to the tricycle in compound 6 (Scheme 2) to natural products of compounds 1-3 lies in the formation of the unusual 7-methoxy-4,5-dihydrooxepin-2(3H)-one ring (ring C). Embedded within this ring is an acyl ketene acetal that is potentially labile to both acid and base, as evidenced by the co-isolation of seco acid derivatives of compounds 1-3 from *Thapsia* sp. as disclosed in J. J. Rubal, et al., *Phytochemistry* 2007, 68, 2480-2486, the entire contents of which are incorporated herein by reference.

In developing the methods used in the present invention, a retrosynthetic approach was considered in which the C ring may be prepared by a formal [5+2] annulation process of advanced tricycle compound 6 and methoxyacetylene, or a suitable derivative, leading directly to the natural products (Scheme 2). Continuing with the retrosynthetic approach, a method of forming the tricycle compound 6 was investigated in which a tandem Claisen/Diels-Alder sequence is performed on the ester compound 7. It was found from this approach that with an available late stage construction of ring C, variants of this ester (e.g., compounds 7a and 7b of Scheme 2) prepared from geraniol derivatives may provide rapid, synthetic access to a number of basiliolide and transtaganolide products.

Scheme 2-Retrosynthetic Reaction

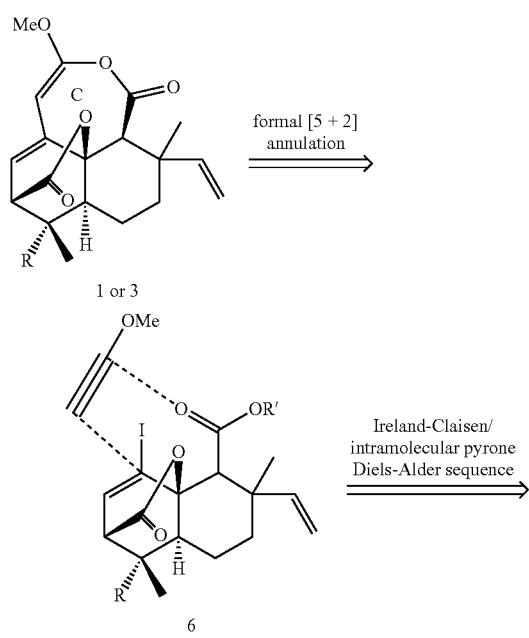

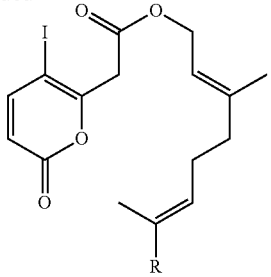

7a, R = Me
7b, R = CO$_2$Me

To build the C ring, strategies involving palladium-mediated cross-coupling reactions were considered, and resulted in the synthesis of compounds of Formula I, including synthetic transtaganolides and basiliolides. Accordingly, aspects of the present invention are directed to synthetic compounds represented by Formula I, and methods of synthesizing those compounds.

In some embodiments, a synthetic compound is represented by Formula I below. In some exemplary embodiments, the synthetic compound of Formula I substantially replicates a basiliolide or transtaganolide natural product.

Formula I

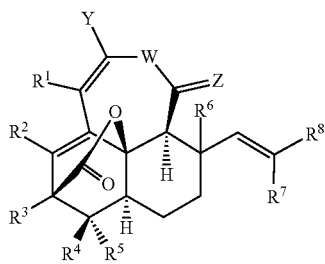

Formula I

In some embodiments of the present invention, a synthetic compound represented by Formula I is provided where Y, W, Z and $R^1$ through $R^8$ are defined as follows:

Y is selected from —$OR^9$, —$NR^{10}R^{11}$, $SR^{12}$, where $R^9$, $R^{10}$, $R^{11}$, and $R^{12}$ are independently selected from hydrocarbyl, substituted hydrocarbyl, heteroatom-containing hydrocarbyl, or substituted heteroatom-containing hydrocarbyl, where any two adjacent R groups of $R^9$, $R^{10}$, $R^{11}$, and $R^{12}$ may optionally form a ring.

W is selected from —O, —S, or —$NR^{21}$, where $R^{21}$ is a hydrogen, hydrocarbyl, substituted hydrocarbyl, heteroatom-containing hydrocarbyl, or substituted heteroatom-containing hydrocarbyl.

Z is selected from —O, —S, or —$NR^{22}$, where $R^{22}$ is hydrogen, hydrocarbyl, substituted hydrocarbyl, heteroatom-containing hydrocarbyl, or substituted heteroatom-containing hydrocarbyl.

$R^1$, $R^2$, and $R^3$ are independently selected from a hydrogen, hydrocarbyl, substituted hydrocarbyl, heteroatom-containing hydrocarbyl, or substituted heteroatom-containing hydrocarbyl, where any two adjacent R groups of $R^1$, $R^2$, and $R^3$ may optionally form a ring.

$R^4$, $R^5$, and $R^6$ are independently selected from hydrogen, hydrocarbyl, substituted hydrocarbyl, heteroatom-containing hydrocarbyl, or substituted heteroatom-containing hydrocarbyl, where two adjacent R groups of $R^4$, $R^5$, and $R^6$ may optionally form a ring.

$R^7$ and $R^8$ are independently selected from hydrogen, hydrocarbyl, substituted hydrocarbyl, heteroatom-containing hydrocarbyl, or substituted heteroatom-containing hydrocarbyl, where two adjacent R groups of $R^7$ and $R^8$ may optionally form a ring.

In other embodiments of the present invention, a synthetic compound of Formula I is provided, where $R^4$, $R^5$ and $R^6$ are independently selected from —$OR^{23}$, —$NR^{24}R^{25}$, $SR^{26}$, where $R^{23}$, $R^{24}$, $R^{25}$, and $R^{26}$ are independently selected from hydrogen, hydrocarbyl, substituted hydrocarbyl, heteroatom-containing hydrocarbyl, or substituted heteroatom-containing hydrocarbyl, where any two adjacent R groups $R^4$, $R^5$, $R^6$, $R^{23}$, $R^{24}$, $R^{25}$, and $R^{26}$ may optionally form a ring.

In some embodiments of the present invention, a synthetic compound of Formula I is provided, where $R^4$ is a hydrogen or methyl, $R^5$ is methyl, —$CH_2OAc$, or —$CO_2CH_3$, and $R^6$ is hydrogen.

In some embodiments of the present invention, a synthetic compound of Formula I is provided, where $R^4$ is —$CO_2CH_3$, —$CH_2OAc$ or —$C(O)N$—$(CH_3)(OCH_3)$ and $R^5$ is methyl.

In other embodiments of the present invention, a synthetic compound of Formula I is provided, where $R^7$ and $R^8$ are independently selected from $SiR^{27}R^{28}R^{29}$, wherein $R^{27}$, $R^{28}$, and $R^{29}$ are independently selected from hydrogen, hydrocarbyl, substituted hydrocarbyl, heteroatom-containing hydrocarbyl, or substituted heteroatom-containing hydrocarbyl, where two adjacent R groups may optionally form a ring. In some embodiments, $R^7$ is a hydrogen and $R^8$ is $SiMe_3$.

In some embodiments, a synthetic composition of transtaganolide C and transtaganolide D, includes synthetic compounds of Formula I, where Y is —OMe, W is oxygen, Z is oxygen, $R^1$, $R^2$, and $R^3$ are each a hydrogen, $R^4$, $R^5$, and $R^6$ are each methyl, and $R^7$ and $R^8$ are each a hydrogen.

In some embodiments of the present invention, a synthetic composition of basiliolide B and epi-8-basiliolide B, includes synthetic compounds of Formula I, where Y is —OMe, W is oxygen, Z is oxygen, $R^1$, $R^2$, and $R^3$ are each hydrogen, $R^4$ is methyl, $R^5$ is —$CO_2Me$, $R^6$ is methyl, and $R^7$ and $R^8$ are each a hydrogen.

In an alternate embodiment, derivatives of Formula I are provided. These derivatives are useful for structure-function analysis in view of the transtaganolide and basiliolide compounds. In some embodiments, these derivatives are represented by a compound of Formula IV.

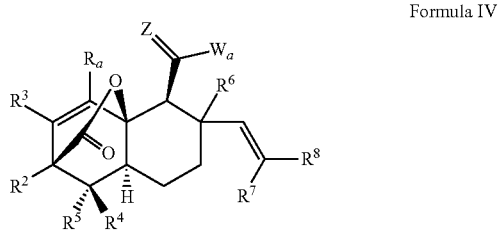

Formula IV

Formula IV is defined as follows, wherein $R^2$ through $R^8$ are defined above with respect to Formula I, and wherein $R_a$ and $W_a$ are defined as follows.

$R_a$ is independently selected from a hydrocarbyl substituted hydrocarbyl, heteroatom-containing hydrocarbyl, or substituted heteroatom-containing hydrocarbyl, where it may optionally form a ring with any adjacent R group. In other embodiments, $R_a$ is an alkoxy or silyl ether moiety. In other embodiments, $R_a$ is vinyl (ethylene), ethoxyacetylene, or methoxy.

$W_a$ is selected from —$OR^x$, —$SR^{xx}$, or —$NR^{xxx}R^{xxxx}$, where each of $R^x$, $R^{xx}$, $R^{xxx}$, and $R^{xxxx}$ is independently selected from hydrogen, hydrocarbyl, substituted hydrocarbyl, heteroatom-containing hydrocarbyl, or substituted heteroatom-containing hydrocarbyl. In other embodiments $W_a$ is tert-butyl dimethylsilyl (TBS), tetramethylsilane (TMS), or OMe.

Any two or more of $R_a$ and $R^3$ through $R^8$ optionally combine to form a ring.

I. Synthesis of Synthetic Compounds of Formula I

In some embodiments of the present invention, a method of synthesizing a compound of Formula I is provided. As shown below in Scheme 3, the method includes reacting a compound of Formula II and a compound of Formula III.

Scheme 3:

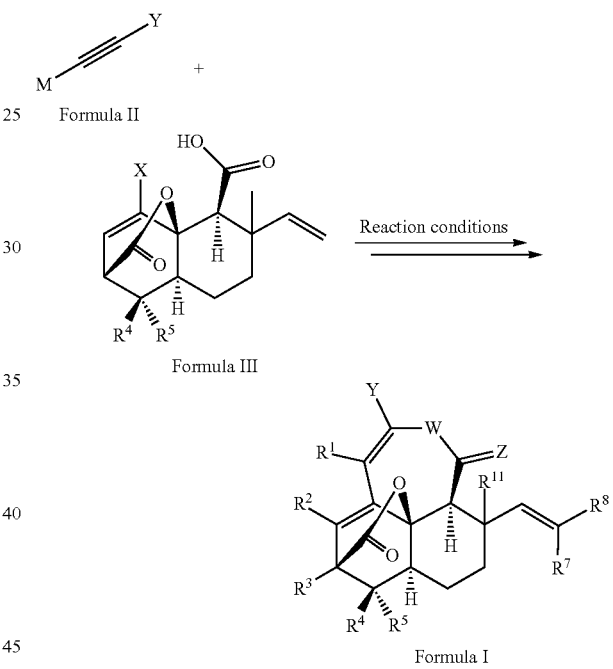

In some embodiments of the present invention, a method of synthesizing a compound of Formula I as defined above, is provided as shown in Scheme 3 above, the method including reacting a compound of Formula II with a compound of Formula III, where M is selected from Li, Na, hydrogen, $SiR^{13}R^{14}R^{15}$, $SnR^{16}R^{17}R^{18}$, $BR^{19}R^{20}$, $ZnX_2$ or $MgX_2$, where $R^{13}$, $R^{14}$, $R^{15}$, $R^{16}$, $R^{17}$, and $R^{18}$ are independently selected from hydrocarbyl or substituted hydrocarbyl; $R^{19}$ and $R^{20}$ are independently selected from hydrogen, hydrocarbyl, substituted hydrocarbyl, heteroatom-containing hydrocarbyl, or substituted heteroatom-containing hydrocarbyl, where two or more adjacent R groups may optionally form a ring, and X is any halogen.

In some embodiments of the present invention, a compound of Formula II and a compound of Formula III are reacted In the presence of a palladium catalyst (e.g., $Pd(PPh_3)_4$ or $Pd(Pt-Bu_3)_2$) in a suitable solvent, at a suitable temperature for the reagents. Examples of solvents include, but are not limited to, dimethylformamide (DMF), THF, acetonitrile, dichloromethane, dichloroethane, toluene, benzene, diethyl ether, DMSO, water, DME, DMA, cyclohexane, t-butyl methylether, carbon tetrachloride, chloroform, methanol, ethanol, heptane, pentane, hexanes, and combinations thereof. As discussed above, temperature may vary depending on the reagents and solvents selected.

A. Compounds of Formula III

In some embodiments of the present invention, a compound of Formula III is prepared by any suitable method or methods. The reagents and methods disclosed herein can be modified by a person having ordinary skill in the art in view of the references incorporated herein. For example, in some embodiments, a compound of Formula III is synthesized following the reaction shown in Scheme 4 below.

Scheme 4:

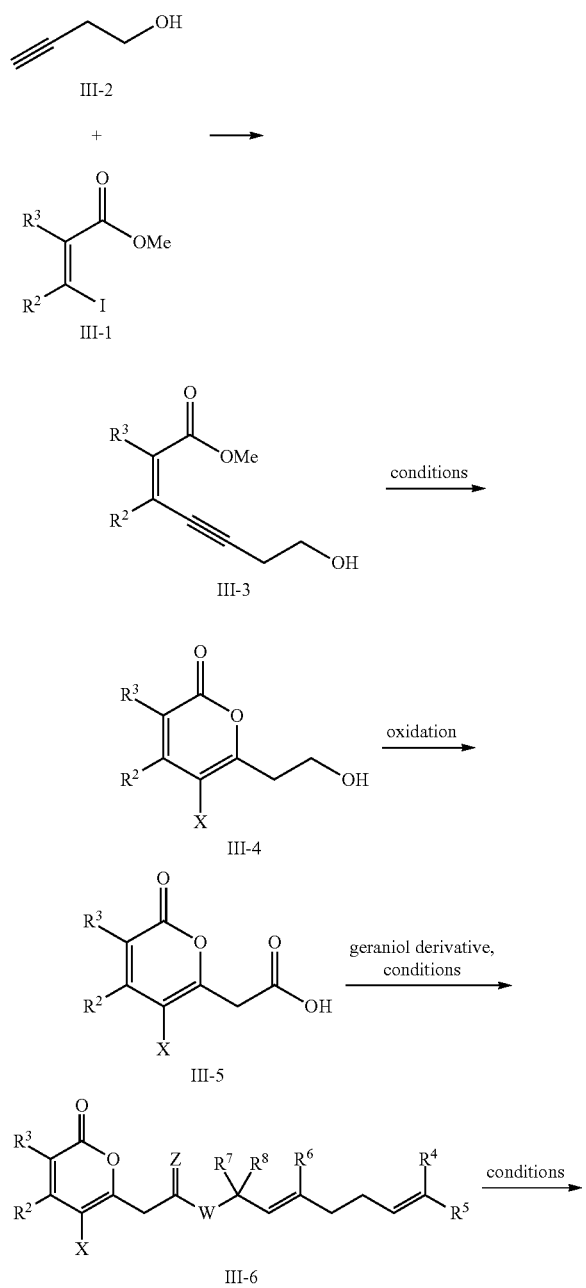

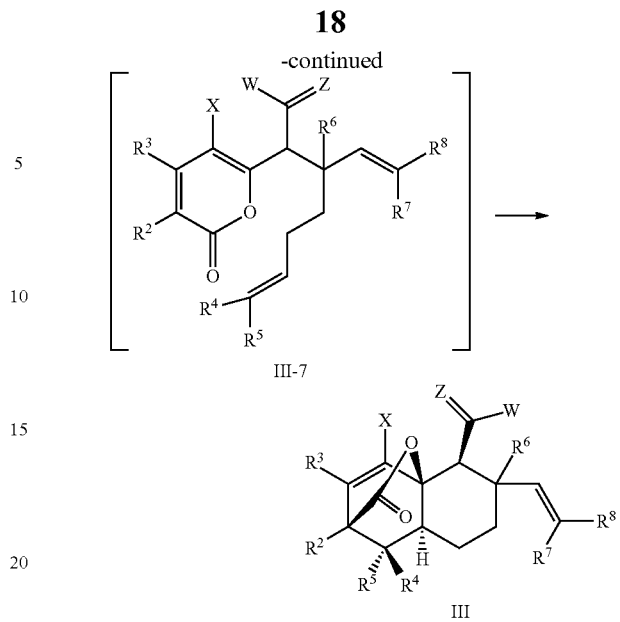

Referring to Scheme 4 above, in some embodiments, a compound of Formula III-1 is reacted with a compound of Formula III-2 in the presence of a palladium catalyst and a solvent. In other embodiments, the palladium catalyst is Pd(PPh$_3$)$_4$ or Pd(Pt-Bu$_3$)$_2$). In some embodiments the reaction is carried out in the presence of triethylamine and/or copper iodide (CuI) in addition to the solvent. This reaction results in the formation of a compound of Formula III-3.

Then, the compound of Formula III-3, is reacted with Cy$_2$NH.HCl or Cy$_2$NH.HBr in the presence of dichloroethane or dibromoethane. In some embodiments, the reaction occurs at 80° C. for 12 hours. This reaction results in the formation of a compound of Formula III-4 (in which X is either Cl or Br).

Alternatively, the compound of Formula III-3 may be reacted with I$_2$ or ICl in a solvent. In some embodiments the solvent is a dichloromethane (DCM). In some embodiments, the reaction occurs at 25° C. for 0.5-4 hours. This results in the formation of compound of Formula III-4 in which X is I.

The compound of Formula III-4 is then oxidized, for example, via a Jones oxidation reaction using chromium trioxide in a dilute sulfuric acid. This results in the formation of compound of Formula III-5.

Next, the compound of Formula III-5 may be reacted with a geraniol derivative in the presence of a solvent. For example, a compound of Formula III-5 may be reacted with a geraniol derivative in DCC (dicyclohexylcarbodiimide) and acetonitrile (MeCN) at 0 to 25° C. Examples of geraniol derivatives include, but are not limited to: (2Z,6E)-methyl 8-hydroxy-2,6-dimethylocta-2,6-dienoate; (2E,6E)-methyl 8-hydroxy-2,6-dimethylocta-2,6-dienoate; (2E,6E)-8-hydroxy-2,6-dimethylocta-2,6-dien-1-yl acetate; (2Z,6E)-8-hydroxy-2,6-dimethylocta-2,6-dien-1-yl acetate; (2Z,6E)-8-hydroxy-N-methoxy-N,2,6-trimethylocta-2,6-dienamide; (2Z,6E)-2,6-dimethylocta-2,6-diene-1,8-diol; (2Z,6E)-2,6-dimethylocta-2,6-diene-1,8-diol; (2E,6E)-8-hydroxy-2,6-dimethylocta-2,6-dienal; and (2Z,6E)-8-hydroxy-2,6-dimethylocta-2,6-dienal. This results in the formation of the compound of Formula III-6.

Then, the compound of Formula III-6 is mixed with water in an aqueous work up. As a result, a transitional compound of Formula III-7 is formed, which then transitions to the compound of Formula III.

Further details regarding the reactions depicted in Scheme 4 can be found in Larock, *J. Org. Chem.* 2003, 68, 5936-5942; Li, *Synthesis,* 2007, 3, 400-406; H. M. Nelson et al., 2009, supra; and Johansson et al., 2009, supra, the entire contents of all of which are incorporated herein by reference.

Previous attempts to couple certain stannane compounds to iodoacid 6a were unsuccessful under standard cross-coupling conditions. (H. M. Nelson, et al., 2009, supra, and R. Larsson et al., 2009, supra.). Accordingly, a suitable protecting group strategy would need to be devised for the carboxylic acid moiety of the Formula III compound. In accordance with the present invention, silyl esters were investigated for this purpose. In some embodiments, for example, tert-butyl dimethylsilyl (TBS)-ester 6b is synthesized by treatment with TBSCl and imidazole, as shown in Scheme 5, below (E. J. Corey et al., *J. Am. Chem. Soc.* 1972, 94, 6190-6191, the entire contents of which are incorporated herein by reference). In some embodiments, the silyl ester is prepared directly from iodoacid 6a (X=I) under slightly modified reaction conditions, i.e. using N,O-bis(tert-butyldimethylsilyl) acetamide. However, the yield over three steps may be significantly lower; ca. 10%.

Scheme 5:

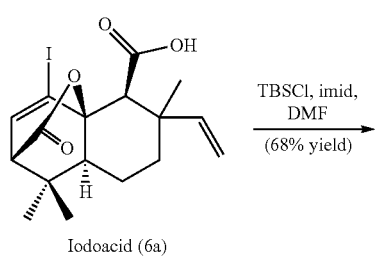

Iodoacid (6a)

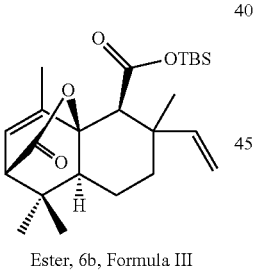

Ester, 6b, Formula III

In other embodiments of the present invention, a compound of Formula III is prepared following a reaction analogous to Scheme 3 above in which compound III-7 includes a trimethylsilyl ($SiMe_3$) protecting group, resulting in a compound of Formula III, where $R^8$ is $SiMe_3$, as shown in Scheme 6a. In some embodiments, compound III-7 ($SiMe_3$) is reacted with BTSA (bis-trimethylsilyl acetamide), and triethylamine ($NEt_3$) in toluene at 100° C., as shown in Scheme 6b, below. In other embodiments compound III-7 ($SiMe_3$) is enantioenriched and chirality is transferred through the cyclization reaction to produce optically active, enantioenriched compound III (90%), as shown in Scheme 6b. In some embodiments the $SiMe_3$ is removed, for example, by treatment with aqueous hydrogen tetrafluoroborate ($HBF_4$) as shown in Scheme 6c.

Scheme 6a:

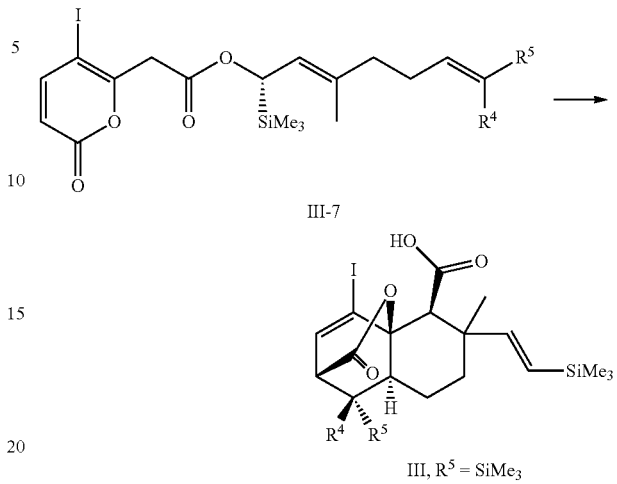

III, $R^5$ = $SiMe_3$

Scheme 6b:

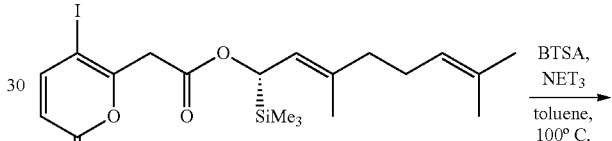

90% ee

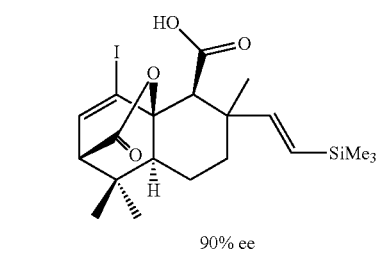

90% ee

Scheme 6c:

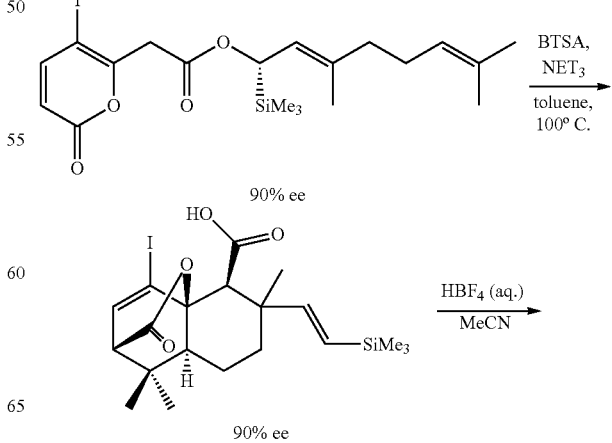

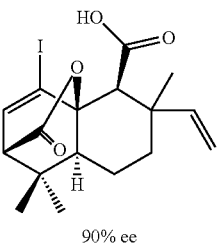

90% ee

In some embodiments of the present invention, a method of enriching for an enantiomer of Formula I is provided, including synthesizing a compound of Formula III in which one of $R^{7'}$ and $R^{8'}$ is a silyl group and the other of $R^{7'}$ and $R^{8'}$ is hydrogen, followed by removal of the silyl group to form an enantioselective compound, and then reacting the compound of Formula II with the enantioselective compound, as shown in Scheme 7, below.

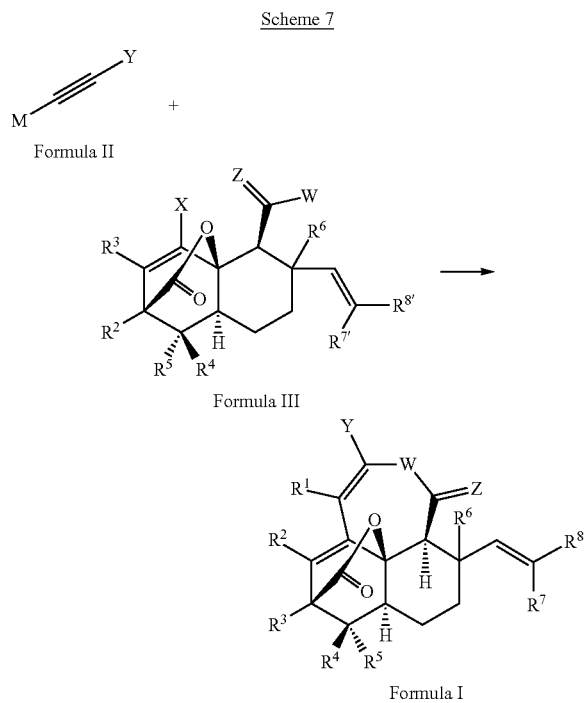

B. Compounds of Formula II

No successful cross-coupling reactions of methoxyacetylene or derivatives thereof to any vinyl or aryl halide have been reported. Accordingly, to utilized a cross-coupling reaction to form the compound of Formula I, a different cross-coupling reactant would be needed. To that end, considering certain limited reports of tin and zinc derivatives of commercial ethoxyacetylene in palladium-catalyzed cross-couplings, the present inventors devised a stannane-based methoxyacetylene derivative in the cross-coupling reactions described herein with respect to the formation of the compound of Formula I. In some embodiments of the present invention, therefore, the compound of Formula I may be made following the reaction in Scheme 8 below. The limited reports of tin and zinc derivatives of commercial ethoxyacetylene in palladium-catalyzed cross-couplings can be found in J. A. Marshall in *Organometallics in Synthesis: A Manual* (Ed.: M. Schlosser) John Wiley & Sons Ltd., West Sussex, 2002, pp. 457; T. Sakamoto et al., *Synlett* 1992, 6, 502; T. Sakamoto, et al., *Chem. Pharm. Bull*, 1994, 42, 2032-2035; A. Löffler et al., *Synthesis* 1992, 5, 495-498, the entire contents of all of which are incorporated herein by reference.

Scheme 8:

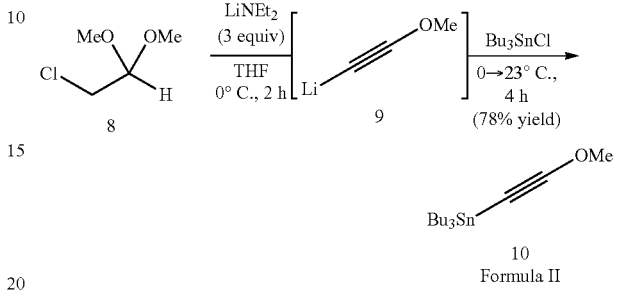

As shown in Scheme 8 above, when exposed to $LiNEt_2$ (lithium diethylamine) in THF (tetrahydrofuran), 1,1-dimethoxy-2-chloro-acetaldehyde (compound 8) is transformed into lithium acetylide (compound 9), which can be quenched with tributyltin chloride ($Bu_3SnCl$) to safely produce a stannane-based derivative of methoxyacetylene (compound 10) (Formula II) at 78% yield in a single operation. An analogous preparation of a lithioethoxyacetylide is reported in S. Raucher et al., *J. Org. Chem.* 1987, 52, 2332-2333, the entire contents of which are incorporated herein by reference. In some embodiments, $Bu_3SnCl$ is substituted with $ZnCl_2$ as further detailed in Example 8 ($Bu_3SnCl$) and Example 9 ($ZnCl_2$) (Negishi coupling). In other embodiments, cross-coupling can be carried out using any suitable method—i.e., any of the standard Pd catalyzed cross-couplings. Examples of Pd-catalyzed cross-coupling methods known in the art include: H (Sonigashira), ZnX (Negishi), $SnR_3$ (Stille), MgX (Kumada), and $BR_3$ (Suzuki).

With reference to Scheme 9 below, exposure of silyl ester 6b and stannane-based compound 10 to $Pd(PPh_3)_4$ or $Pd(Pt-Bu_3)_2$ leads to transient formation of an enzyme 11. The Pd(PT-Bu3)2 catalyst is disclosed in C. Dai, g. C. Fu, *J. Am. Chem. Soc.* 2001, 122, 2719-2724, the entire contents of which are incorporated herein by reference. While observable by mass spectrometry and $^1H$ NMR analysis, direct isolation of the methoxyenyne compound 11 proved difficult. After optimization of the reaction conditions, aqueous work-up effected in situ desilylation and cyclization to afford a separable mixture of transtaganolide C (1a) and transtaganolide D (1b) at 21% and 10% yield, respectively, using $Pd(PPh_3)_4$ catalyst (19% and 10% with $Pd(Pt-Bu_3)_2$ catalyst). Screening of reaction conditions failed to improve the yields of transtaganolides 1a and 1b. The difficulty in achieving an efficient [5+2] annulation is attributed to several factors. It was found that the methoxyenyne compound 11 is unstable under the reaction conditions—i.e., modest extension of the reaction time (~24 h) leads to non-productive consumption of the intermediate methoxyenyne compound 11. Additionally, the stannane-based compound 10 is itself unstable to Pd catalysis: addition of $Pd(PPh_3)_4$ to a solution of the stannane-based compound 10 in DMF (dimethylformamide) leads to consumption of the stannane-based compound 10 and the formation of oligomeric products.

Scheme 9:

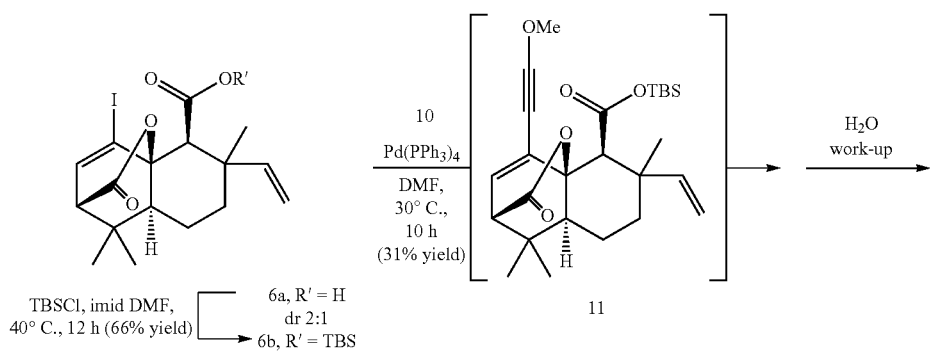

The relative stereochemistry of synthetic transtaganolide C (1a) of Formula I (Scheme 9) was unambiguously confirmed by X-ray crystallography, and synthetic transtaganolides C and D were spectroscopically indistinguishable from the naturally occurring isolates (FIGS. 1-4; Appendix). Crystallographic data (Appendix), have been deposited at the CCDC, 12 Union Road, Cambridge CB2 1EZ, UK under the deposition number 796908.

With reference to Scheme 10 below, basiliolide B (3a) of Formula I, was synthesized using known geraniol derivative 12. Synthesis of the geraniol derivative 12 is disclosed in H. Shibuya et al., *Chem. Pharm. Bull.* 1994, 42, 293-299, the entire contents of which are incorporated herein by reference. In synthesizing the basiliolide B (3a), the geraniol derivative (compound 12) was first coupled to an acid functional iodopyrone (compound 13) to form an ester compound (ester compound 7b) at high yield. This reaction is discussed in H. M. Nelson et al., 2009, supra, and R. Larsson et al., 2009, supra.

Continuing in the synthesis of basiliolide B, the ester 7b is treated with N,O-bis(trimethylsilyl)acetamide (BSA or BTSA) and triethylamine (NEt$_3$), which resulting a Claisen/Diels-Alder cascade to yield the resulting acid 6c (a compound of Formula III), in a single operation and in 67% yield as a 2:1 mixture of diastereomers, as shown in Scheme 10.

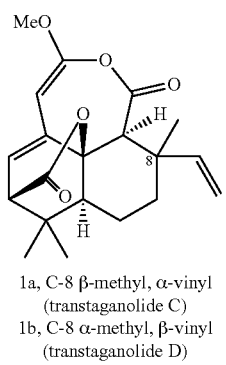

1a, C-8 β-methyl, α-vinyl
(transtaganolide C)
1b, C-8 α-methyl, β-vinyl
(transtaganolide D)

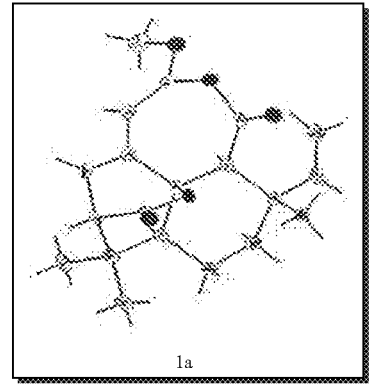

1a

Scheme 10:

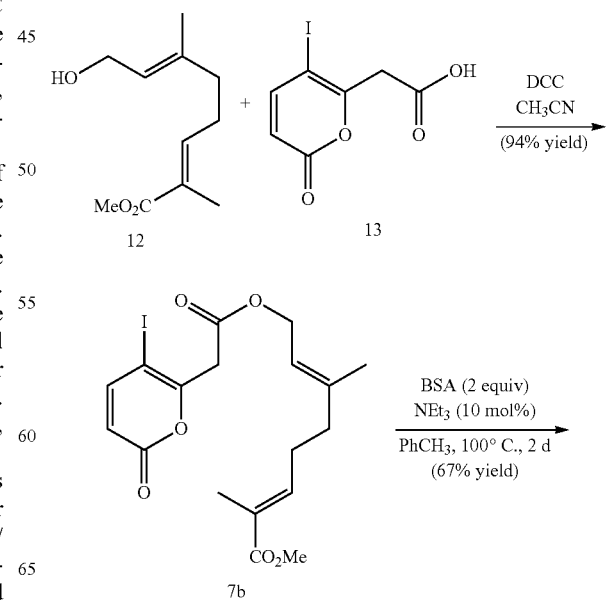

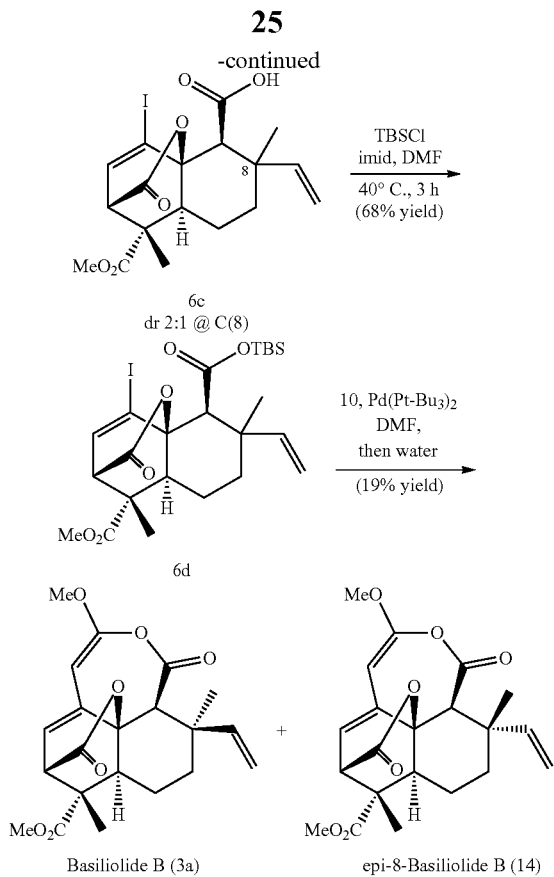

6c
dr 2:1 @ C(8)

6d

Basiliolide B (3a) + epi-8-Basiliolide B (14)

Lowering the concentration of the ester in the reaction allowed for the Diels-Alder cycloaddition to occur in the same reaction mixture. Alternatively, microwave irradiation of the intermediate acid in $CH_2Cl_2$ in a sealed vial at 165° C. for 48 hours also smoothly produces the Diels-Alder product. This represents an improvement over previous, two-step procedures that required isolation and/or manipulation of the Claisen products (e.g. Scheme 1), and is the first example in this area that utilizes a more functionalized dienophile.

With reference to Scheme 10, following silylation of the free acid in compound 6c to form compound 6d, the resulting silyl ester (compound 6d) was exposed to the presently disclosed methoxy-alkynylation reactants including stannane-based compound 10 and $Pd(Pt-Bu_3)_2$. Further details of the silylation reaction made be found in T. P. Mawhinney et al., *J. Org. Chem.* 1982, 47, 3336-3339, the entire contents of which are incorporated herein by reference. The cross-coupling of compound 6d with compound 10, and the subsequent treatment with water of the crude product yield resulted in the production and isolation of synthetic basiliolide B (compound 3a) and previously unreported epi-8-basiliolide B (compound 14) in 5% and 14% yields, respectively, using $Pd(PPh_3)_4$ (6% and 12% with $Pd(PPh_3)_4$). The isolated synthetic basiliolide B (3a) was spectroscopically indistinguishable from the natural product isolated from *Thapsia* sp (FIGS. 5-6; Appendix).

II. Synthesis of Compounds of Formula IV

In some embodiments of the present invention, compounds of Formula IV are synthesized for use in structure-function assays in view of the characterized potential of the transtaganolide and basiliolide compounds. In some embodiments, compounds of Formula IV are synthesized according to the reaction shown in Scheme 11, below.

Scheme 11:

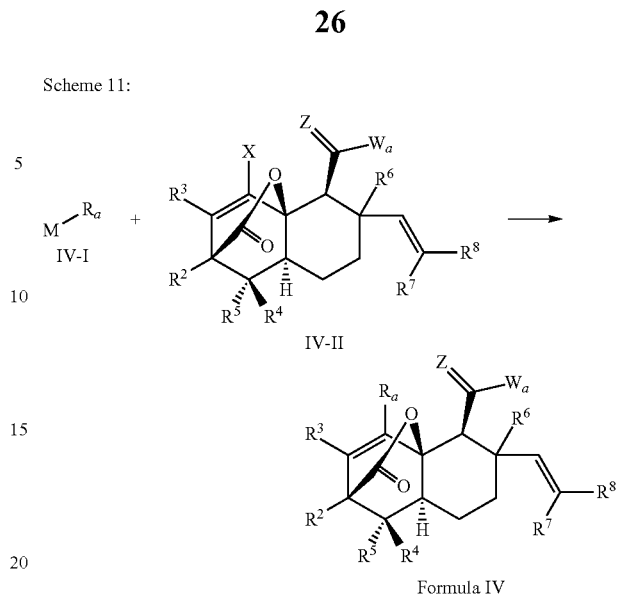

Formula IV

With reference to Scheme 11, a compound of Formula IV-I is reacted with a compound of Formula IV-II to form a compound of formula IV, wherein:

$R_a$ is selected from the group consisting of hydrocarbyl, substituted hydrocarbyl, heteroatom-containing hydrocarbyl, and substituted heteroatom-containing hydrocarbyl;

$W_a$ is selected from the group consisting of $-OR^X$, $-SR^{XX}$, and $-NR^{XXX}R^{XXXX}$, where each of $R^X$, $R^{XX}$, $R^{XXX}$ and $R^{XXXX}$ is independently selected from the group consisting of hydrogen, hydrocarbyl, substituted hydrocarbyl, heteroatom-containing hydrocarbyl, and substituted heteroatom-containing hydrocarbyl;

each of $R^3$ through $R^8$ is selected from the group consisting of hydrogen, hydrocarbyl, substituted hydrocarbyl, heteroatom-containing hydrocarbyl, and substituted heteroatom-containing hydrocarbyl;

Z is selected from the group consisting of —O, —S and $-NR^{22}$, wherein $R^{22}$ is selected from the group consisting of hydrocarbyl, substituted hydrocarbyl, heteroatom-containing hydrocarbyl, and substituted heteroatom-containing hydrocarbyl;

M is selected from the group consisting of Li, Na, hydrogen, $SiR^{12}R^{14}R^{15}$, $SnR^{16}R^{17}R^{18}$, $BR^{19}R^{20}$, $MgX'_2$ and $ZnX''_2$, wherein:

each of $R^{13}$ through $R^{18}$ is independently selected from the group consisting of hydrocarbyl, and substituted hydrocarbyl, each of $R^{19}$ and $R^{20}$ is independently selected from the group consisting of hydrogen, hydrocarbyl, substituted hydrocarbyl, heteroatom-containing hydrocarbyl, and substituted heteroatom-containing hydrocarbyl, and each of X' and X" is independently selected from the group consisting of halogens;

X is a halogen; and any two or more of $R_a$ and $R^3$ through $R^8$ optionally combine to form a ring.

The reaction of Scheme 11 may occur under varying suitable conditions with varying suitable reagents as disclosed herein. For example, the reaction can occur in the presence of a palladium catalyst (e.g., $Pd(PPh_3)_4$ or $Pd(Pt-Bu_3)_2$ in a suitable solvent and temperature. Examples of solvents include, but are not limited to dimethylformamide (DMF), THF, acetonitrile, dichloromethane, dichloroethane, toluene, benzene, diethyl ether, DMSO, water, DME, DMA, cyclohexane, t-butyl methylether, carbon tetrachloride, chloroform, methanol, ethanol, heptane, pentane, hexanes, and combinations thereof. As discussed above, temperature will vary depending on the reagents selected.

Figure 16:
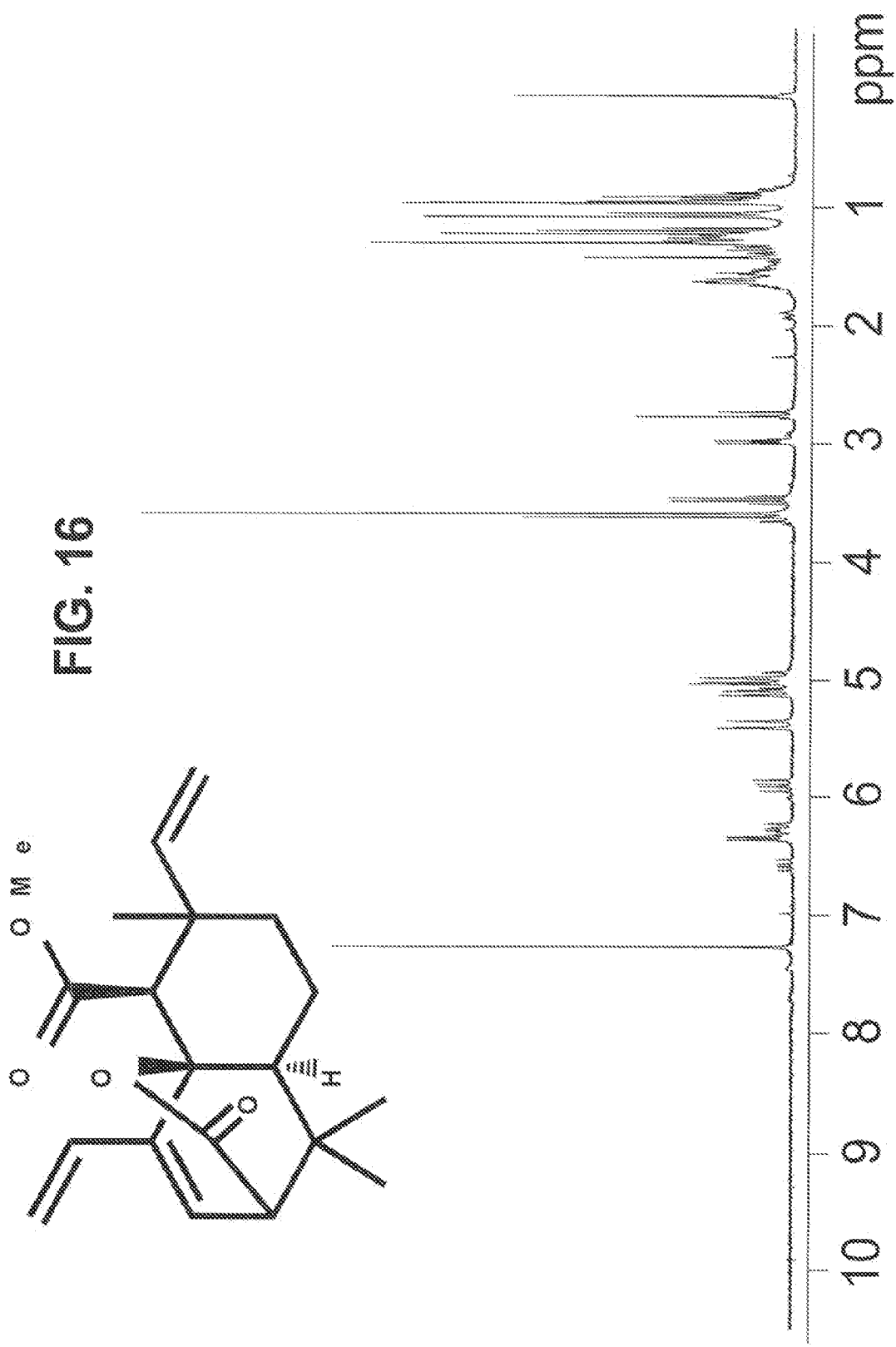
FIG. 16 is a $^1$H NMR spectrum of a representative example of a compound of Formula IV, in which $R_a$ is a vinyl moiety and $W_a$ is methoxy, according to aspects of the present invention.

In some embodiments, a compound of Formula IV in which $R_a$ is a vinyl group and $W_a$ is —OMe (methoxy) is provided. In some embodiments this compound of Formula IV is synthesized following the reaction shown below in Scheme 12. FIG. 16 shows a $^1$H NMR spectrum of this Formula IV compound.

Scheme 12:

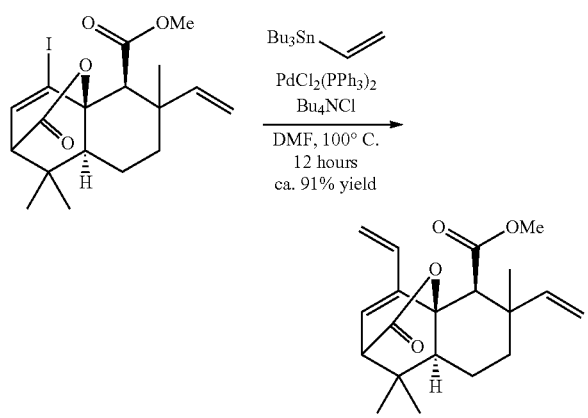

Figure 17:
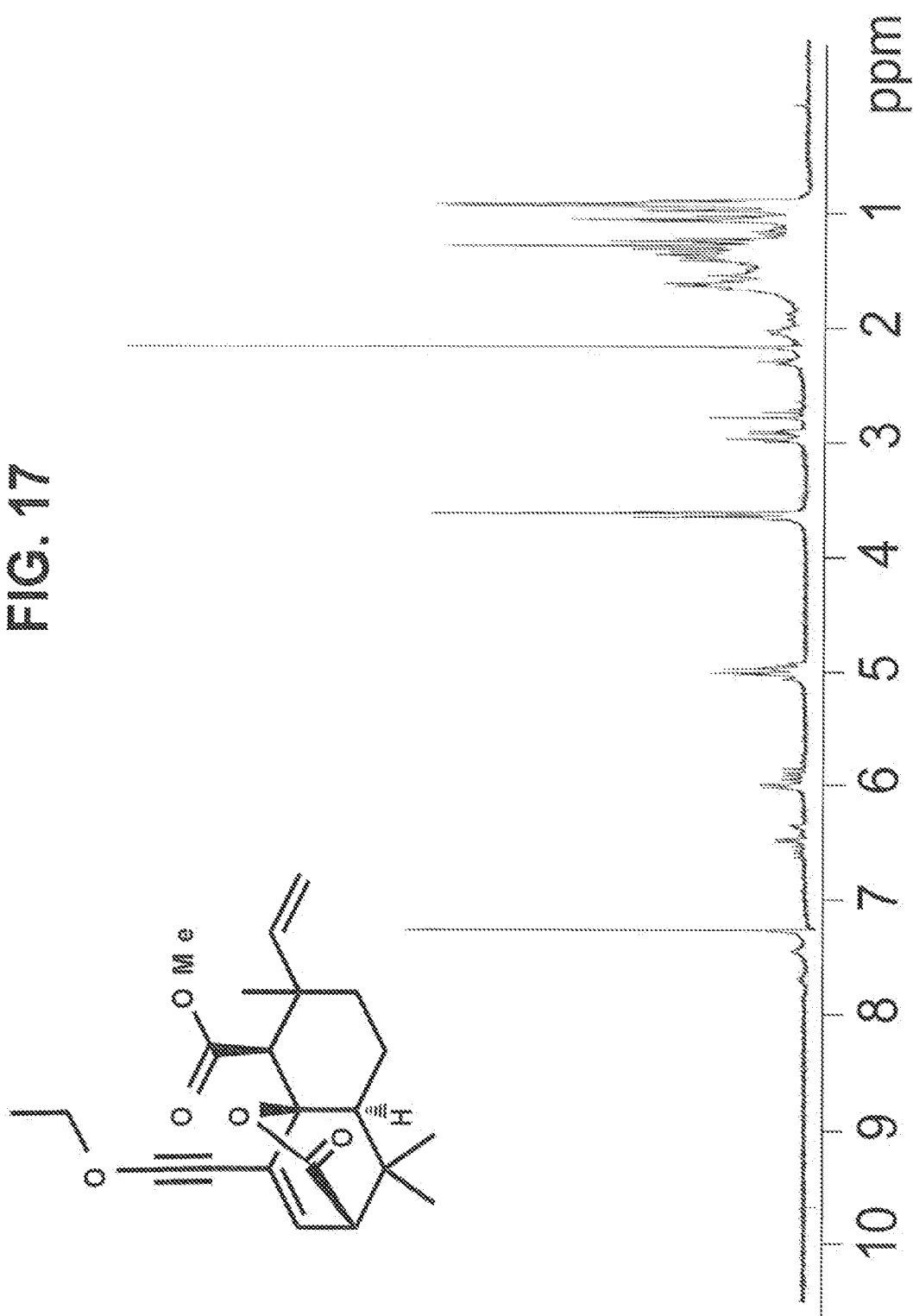
FIG. 17 is a $^1$H NMR spectrum of a representative example of a compound of Formula IV, in which $R_a$ is an ethoxyacetylene moiety and $W_a$ is methoxy, according to aspects of the present invention.

In some embodiments, a compound of Formula IV in which $R_a$ is ethoxyacetylene and $W_a$ is —OMe (methoxy) is provided. In some embodiments this compound of Formula IV is synthesized following the reaction shown below in Scheme 13. FIG. 17 shows a $^1$H NMR spectrum of this Formula IV compound.

Scheme 13:

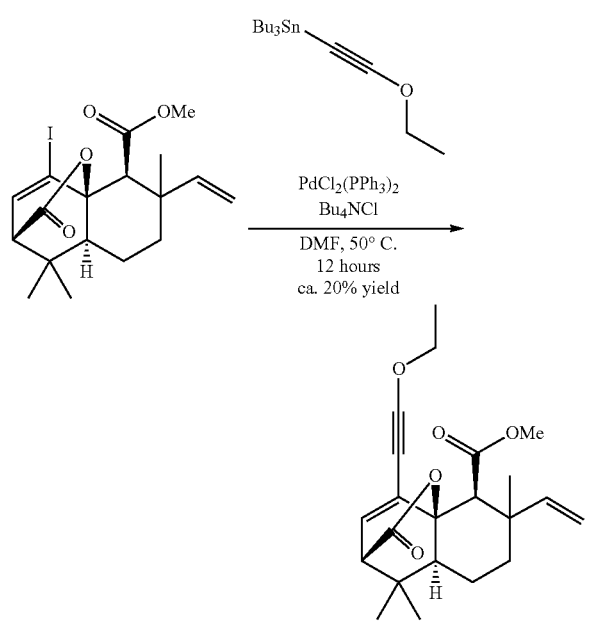

The following Examples are presented for illustrative purposes only, and do not limit the scope or content of the present application.

EXAMPLES

Materials and Methods

Unless otherwise stated, reactions were performed in flame-dried glassware under an argon or nitrogen atmosphere using dry deoxygenated solvents. Solvents were dried by passage through an activated alumina column under argon. Pd(t-Bu$_3$P)$_2$, N,N'-dicyclohexylcarbodiimide, 1,1-dimethoxy-2-chloro-acetaldehyde, N,O-bis(trimethylsilyl)acetamide, N-methyl-N-(tert-butyldimethylsilyl)triflouroacetamide, and imidazole were purchased from Sigma-Aldrich Chemical Company and used as received. Pd(PPh$_3$)$_4$ was prepared using known methods—e.g., M. R. Mason et al., *Organometallics*, 1992, 11, 2212-2220, the entire contents of which is incorporated herein by reference. Thin-layer chromatography (TLC), both preparatory and analytical, were performed using E. Merck silica gel 60 F254 precoated plates (0.25 mm) and visualized by UV fluorescence quenching, p-anisaldehyde, I$_2$, or KMnO$_4$ staining (M. R. Mason et al. 1992, supra). ICN Silica gel (particle size 0.032-0.063 mm) was used for flash chromatography.

$^1$H NMR, and $^{13}$C NMR spectra (FIGS. 1-15), were recorded on a Varian Mercury 300 (at 300 MHz) or on a Varian Unity Inova 500 (at 500 MHz). $^1$H NMR spectra are reported relative to CDCl$_3$ (7.26 ppm). Data for $^1$H NMR spectra are reported as follows: chemical shift, multiplicity, coupling constant (Hz), integration. Multiplicities are reported as follows: s=singlet, d=doublet, t=triplet, q=quartet, sept.=septet, m=multiplet, comp. m=complex multiplet, app.=apparent, bs=broad singlet. $^{13}$C NMR spectra are reported relative to CDCl$_3$ (77.0 ppm).

Fourier Transform Infrared (FTIR) spectroscopy spectra were recorded on a Perkin Elmer SpectrumBX spectrometer and are reported in frequency of absorption (cm$^{-1}$). High Resolution Mass Spectrometry (HRMS) data were acquired using an Agilent 6200 Series TOF with an Agilent G1978A Multimode source in electrospray ionization (ESI), atmospheric pressure chemical ionization (APCI) or multimode-ESI/APCI. Crystallographic data were obtained from the Caltech X-ray Diffraction Facility. FTIR and HRMS data are provided in the Appendix.

Experimental Procedures

Example 1

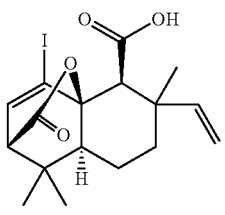

Iodoacid 6a (of Formula III)

Iodoacid 6a. To a solution of 7a (6.2 g, 15 mmol, 1.0 equiv) in toluene (75 mL) at 25° C. in a sealed tube was added N,O-bis(trimethylsilyl)acetamide (BTSA) (7.2 mL, 30 mmol 2.0 equiv). To the reaction mixture was then added triethylamine (0.41 mL, 3.0 mmol, 0.20 equiv). The reaction mixture was heated to 110° C. and stirred for 20 minutes. The mixture was cooled to 25° C. and diluted with toluene (750 mL). The reaction mixture was then re-heated to 100° C. and stirred for 4 days. The mixture was cooled to 25° C. and extracted with saturated aqueous NaHCO$_3$ (7×100 mL). To the combined aqueous extracts was added 1 M aqueous HCl until pH=3. The aqueous layer was then extracted with ethyl acetate (3×100 mL). The combined organics were dried over Na$_2$SO$_4$, and concentrated by rotary evaporation to yield 3.2 g (51%) of 6a as a tan foam.

Major: $^1$H NMR (500 MHz, CDCl$_3$) δ 6.93 (d, J=6.5 Hz, 1H), 6.01 (dd, J=10.5, 17.5 Hz, 1H), 5.05-5.02 (m, 2H), 3.00-2.94 (m, 2H), 1.68-1.42 (m, 5H), 1.29 (s, 3H), 1.08 (s, 3H), 1.00 (s, 3H); $^{13}$C NMR (125 MHz, CDCl$_3$) δ 172.7, 170.5, 148.0, 140.0, 111.5, 97.9, 84.7, 59.4, 56.4, 47.9, 39.8, 36.8, 29.8, 24.5, 20.5, 18.4. Minor: $^1$H NMR (500 MHz, CDCl$_3$) δ 6.93 (d, J=6.5 Hz, 1H), 6.35 (dd, J=11.0, 17.5 Hz, 1H), 5.09 (d, J=11.0 Hz, 1H), 5.05-5.02 (m, 1H), 3.00-2.94 (m, 2H), 1.92-1.90 (m, 1H), 1.68-1.42 (m, 4H), 1.26 (s, 3H), 1.08 (s, 3H), 1.00 (s, 3H).

$^{13}$C NMR (125 MHz, CDCl$_3$) δ 172.7, 170.4, 140.4, 140.3, 113.7, 97.4, 84.8, 61.0, 56.6, 48.0, 39.3, 38.7, 37.0, 29.8, 29.5, 24.5, 20.6. FTIR (Neat Film NaCl) 3081, 2967, 2931, 1754, 1741, 1738, 1732, 1708, 1414, 1396, 1219, 1175, 964, 916, 874, 797, 736 cm$^{-1}$; HRMS (Multimode-ESI/APCI) m/z calc'd for C$_{17}$H$_{21}$O$_4$I [M+H]$^+$: 417.0557, found 417.0553.

Example 2

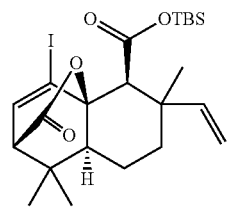

tert-Butyldimethylsilyl ester 6b (of Formula III)

tert-Butyldimethylsilyl ester 6b. To a solution of 6a (46 mg, 0.11 mmol, 1.0 equiv) in dimethylformamide (0.30 mL) were added tert-butyldimethylsilylchloride (84 mg, 0.56 mmol, 5.0 equiv) and imidazole (76 mg, 1.1 mmol, 10 equiv). The reaction was warmed to 40° C. and then stirred for 12 hours. The reaction mixture was then diluted with saturated aqueous NaCl (1 mL) and extracted with diethyl ether/hexane (1:1) (3×2 mL). The combined organic extracts were washed with saturated aqueous KHSO$_4$ (1 mL) and then with saturated aqueous NaCl (3×1 mL). The combined organics were dried over Na$_2$SO$_4$, and concentrated by rotary evaporation. The crude oil was chromatographed (ethyl acetate in hexane 10⇒50% on SiO$_2$) to yield 39 mg (66%) of 6b as a white powder.

Procedure 2. To a solution of 6a (180 mg, 0.43 mmol, 1.0 equiv) in acetonitrile (0.43 mL) was added N-methyl-N-(tert-butyldimethylsilyl)trifluoroacetamide (1.0 g, 4.3 mmol, 10 equiv) at 25° C. and stirred for 15 minutes. The reaction mixture was diluted with saturated aqueous NaCl (1 mL) and extracted with diethyl ether/hexane (1:1) (3×2 mL). The combined organic extracts were washed with saturated aqueous KHSO$_4$ (1 mL) and then with saturated aqueous NaCl (3×1 mL). The combined organics were dried over Na$_2$SO$_4$, and concentrated by rotary evaporator. The crude oil was chromatographed (ethyl acetate in hexane 10⇒50% on SiO$_2$) to yield 150 mg (64%) of 6b as a white powder.

Figure 7:
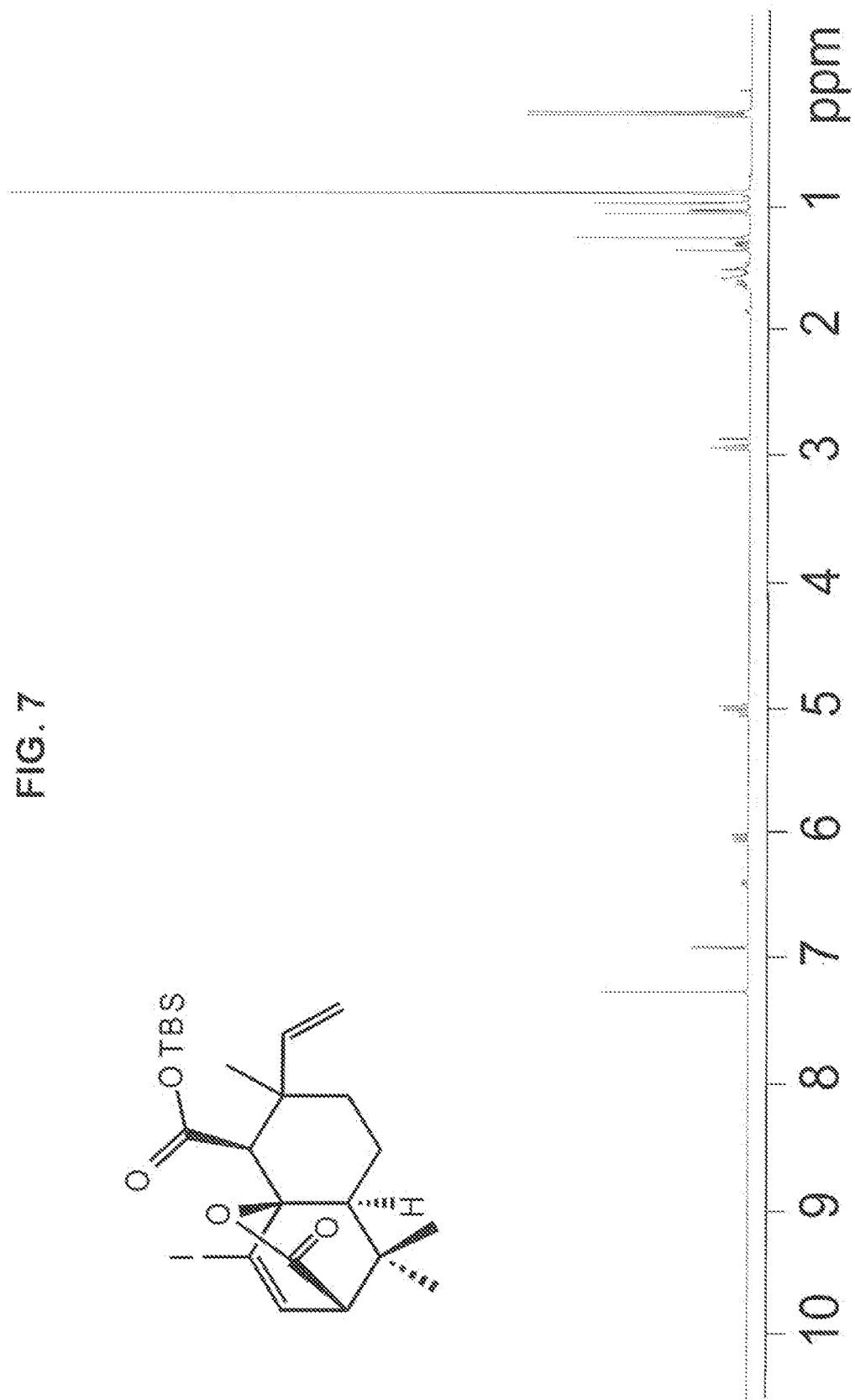
FIG. 7 is a $^1$H NMR spectrum of tert-butyldimethylsilyl ester (6b), according to aspects of the present invention.
Figure 8:
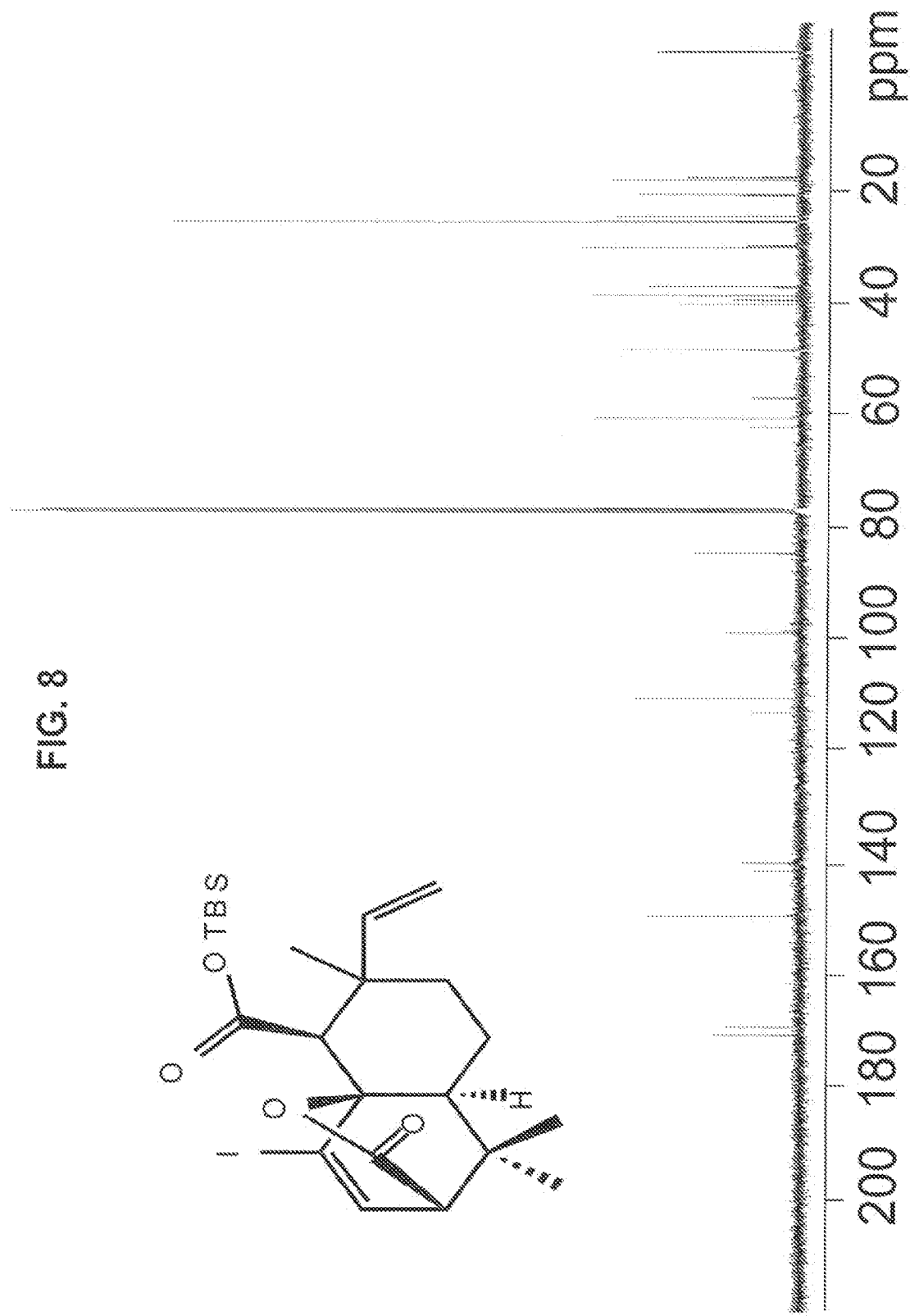
FIG. 8 is a $^{13}$C NMR spectrum of tert-butyldimethylsilyl ester (6b), according to aspects of the present invention.

FIG. 7 shows a $^1$H NMR spectrum for tert-butyldimethylsilyl ester (6b). Major: $^1$H NMR (500 MHz, CDCl$_3$) δ 6.90 (d, J=6.5 Hz, 1H), 6.03 (dd, J=11.0, 17.5 Hz, 1H), 4.99 (d, J=17.5 Hz, 1H), 4.99 (d, J=11.0 Hz, 1H), 2.95 (s, 1H), 2.93 (d, J=6.5 Hz, 1H), 1.66-1.39 (m, 4H), 1.32-1.29 (m, 1H), 1.26 (s, 3H), 1.07 (s, 3H), 0.99 (s, 3H), 0.91 (s, 9H), 0.29 (s, 3H), 0.27 (s, 3H); FIG. 8 shows a $^{13}$C NMR spectrum for tert-butyldimethylsilyl ester (6b). $^{13}$C NMR (125 MHz, CDCl$_3$) δ 170.6, 169.1, 149.2, 139.7, 110.5, 98.7, 84.6, 60.4, 56.7, 48.2, 40.1, 38.7, 36.9, 29.8, 25.5, 24.5, 20.7, 18.1, 17.5, −4.8, −4.8.

Minor: $^1$H NMR (500 MHz, CDCl$_3$) δ 6.90 (d, J=6.5 Hz, 1H), 6.40 (dd, J=11.0, 17.5 Hz, 1H), 5.05 (dd, J=1.0, 11.0 Hz, 1H), 5.03-4.98 (m, 1H), 2.91 (d, J=6.5 Hz, 1H), 2.86 (s, 1H), 1.85 (dt, J=3.5, 13.5 Hz, 1H), 1.66-1.39 (m, 3H), 1.36 (s, 3H), 1.34-1.29 (m, 1H), 1.05 (s, 3H), 0.98 (s, 3H), 0.90 (s, 9H), 0.30 (s, 3H), 0.28 (s, 3H). $^{13}$C NMR (125 MHz, CDCl$_3$) δ 170.6, 169.3, 141.3, 139.9, 112.9, 98.3, 84.7, 61.8, 56.8, 48.4, 39.6, 39.4, 37.2, 29.6, 25.6, 25.4, 24.4, 20.8, 17.5, −4.9, −4.9.

FTIR (Neat Film NaCl) 3959, 2929, 2857, 1760, 1716, 1708, 1471, 1284, 1250, 1173, 1022, 967, 840, 827, 789, 736 cm$^{-1}$. HRMS (Multimode-ESI/APCI) m/z calc'd for C$_{23}$H$_{36}$O$_4$ISi [M+H]$^+$: 531.1422, found 531.1432 (Appendix.)

Example 3

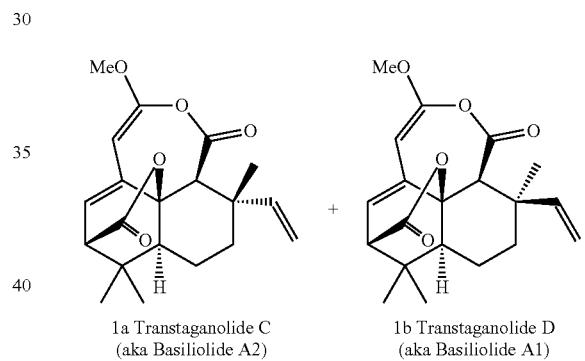

1a Transtaganolide C
(aka Basiliolide A2)

1b Transtaganolide D
(aka Basiliolide A1)

Transtaganolides (1). In a nitrogen filled glovebox, to a solution of 6b (16 mg, 0.030 mmol, 1.0 equiv) and Pd(PPh$_3$)$_4$ (35 mg, 0.030 mmol, 1 equiv) in dimethylformamide (0.30 mL, 0.10 M) was added tributyl(2-methoxyethynyl)stananne (10) (32 mg, 0.090 mmol, 3.0 equiv). The reaction was stirred at 31° C. for 16 h. The reaction mixture was then treated with water (30 µL) and stirred at room temperature for 1 hour. That mixture was diluted with ethyl acetate (1 mL) and washed with water (4×0.5 mL) and concentrated by rotary evaporation. The crude oil was purified by normal phase HPLC to yield 2.1 mg (21%) of transtaganolide C (1a) and 1.1 mg (10%) of transtaganolide D (1b) as white powders. Crystals were grown by slow evaporation from acetonitrile.

Procedure 2. In a nitrogen filled glovebox, to a solution of 6b (16 mg, 0.030 mmol, 1.0 equiv) and Pd(t-Bu$_3$P)$_2$ (15 mg, 0.030 mmol, 1.0 equiv) in dimethylformamide (0.30 mL, 0.10 M) was added tributyl(2-methoxyethynyl)stannane (10) (32 mg, 0.090 mmol, 3.0 equiv). The reaction was stirred at 31° C. for 10 hours. The reaction mixture was then treated with water (30 µL) and stirred at room temperature for 1 hour. The mixture was diluted with ethyl acetate (1 mL) and washed with water (4×0.5 mL) and concentrated by rotary evaporation. The crude oil was purified by normal phase HPLC to yield 2.0 mg (19%) of transtaganolide C (1a) and 1.0 mg (10%) of transtaganolide D (1b) as white powders.

Transtaganolide C (1a). FIG. 1 shows a $^1$H NMR spectrum of Transtaganolide C (1a). $^1$H NMR (500 MHz, CDCl$_3$) δ 6.07 (dd, J=1.5, 6.5 Hz, 1H), 5.80 (dd, J=11.0, 17.5 Hz, 1H), 5.07 (d, J=17.5 Hz, 1H), 5.03 (d, J=11.0 Hz, 1H), 5.00 (d, J=1.5 Hz, 1H), 3.71 (s, 3H), 3.23 (s, 1H), 3.06 (d, J=6.5 Hz, 1H), 1.71-1.63 (m, 3H), 1.60 (s, 3H), 1.44 (m, 1H), 1.30 (m, 1H), 1.08 (s, 3H), 0.97 (s, 3H).

FIG. 2 shows a $^{13}$C NMR spectrum of Transtaganolide C (1a). $^{13}$C NMR (125 MHz, CDCl$_3$) δ 171.8, 162.3, 156.7, 146.5, 138.0, 123.6, 112.8, 87.3, 79.3, 56.3, 53.8, 50.6, 48.1, 38.4, 38.3, 33.3, 29.9, 24.8, 19.9, 19.2.

FTIR (Neat Film NaCl) 2965, 2928, 2872, 1791, 1761, 1668, 1619, 1456, 1334, 1267, 1233, 1178, 1115, 970, 954, 828 cm$^{-1}$. HRMS (Multimode-ESI/APCI) m/z calc'd for C$_{20}$H$_{24}$O$_5$ [M+H]$^+$: 345.1697, found 345.1703; MP: 135-160° C. (at these temperatures decarboxylation is thought to occur, as the crystalline sample and the resulting liquid were vigorously bubbling throughout the measurement, thus it is unclear whether thermal decomposition precluded state change) (Appendix).

Figure 3:
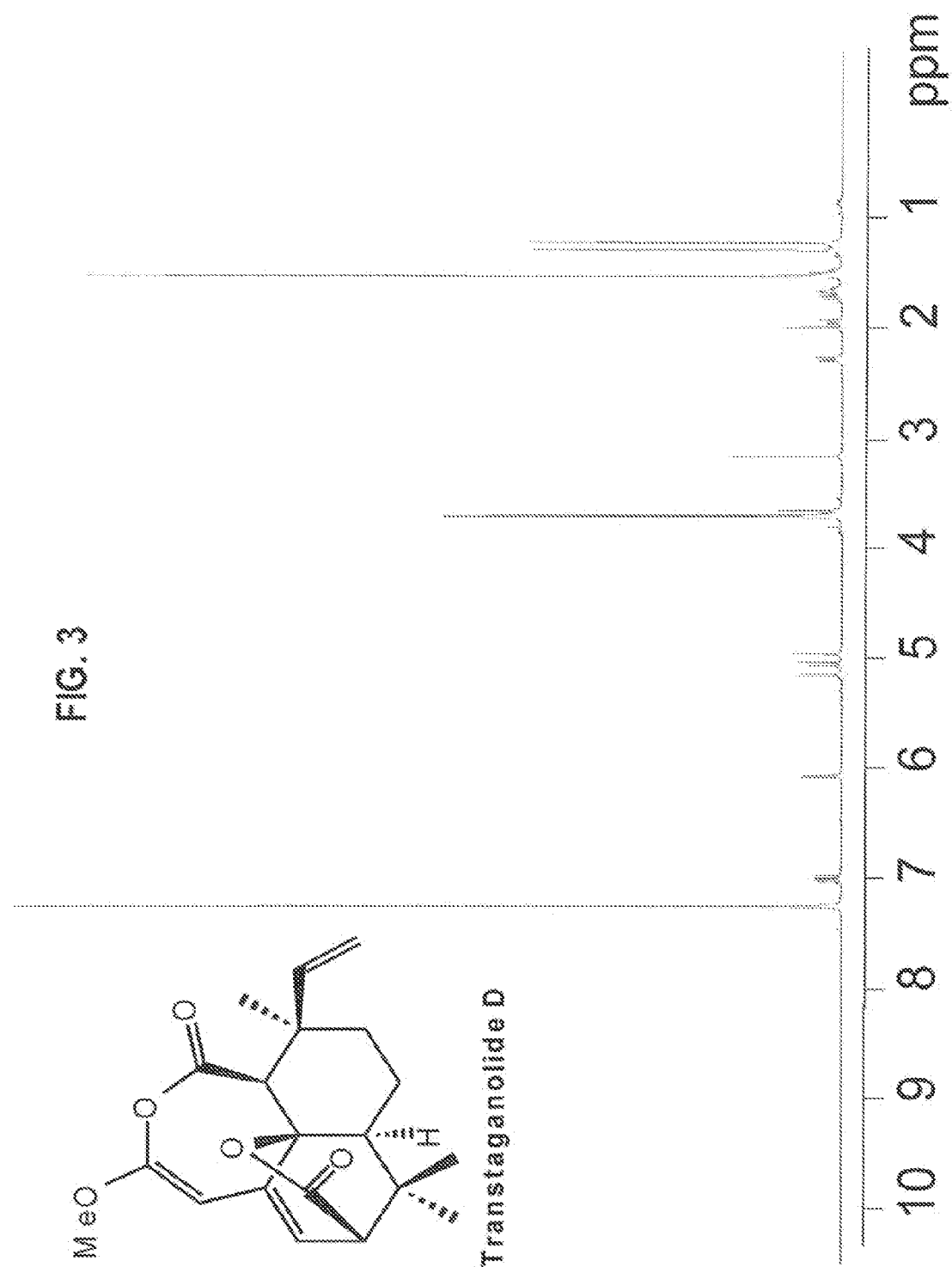
FIG. 3 is a $^1$H NMR spectrum of transtaganolide D (1b), according to aspects of the present invention.

Transtaganolide D (1b). FIG. 3 shows a $^1$H NMR spectrum of Transtaganolide D (1b). $^1$H NMR (500 MHz, CDCl$_3$) δ 7.00 (dd, J=11.0, 17.5 Hz, 1H), 6.09 (dd, J=1.0, 6.5 Hz, 1H), 5.15 (dd, J=1.0, 11.0 Hz, 1H), 5.05 (dd, J=1.0, 17.5 Hz, 1H), 5.02 (d, J=1.0 Hz, 1H), 3.73 (s, 3H), 3.13 (s, 1H), 3.06 (d, J=6.5 Hz, 1H), 1.91 (dt, J=3.5, 13.5 Hz, 1H), 1.64 (dquint, J=3.0, 13.5 Hz, 1H), 1.58 (m, 1H), 1.39 (dt, J=3.5, 13.5 Hz, 1H), 1.33 (dd, J=4.5, 13.5 Hz, 1H), 1.22 (s, 3H), 1.04 (s, 3H), 0.97 (s, 3H).

Figure 4:
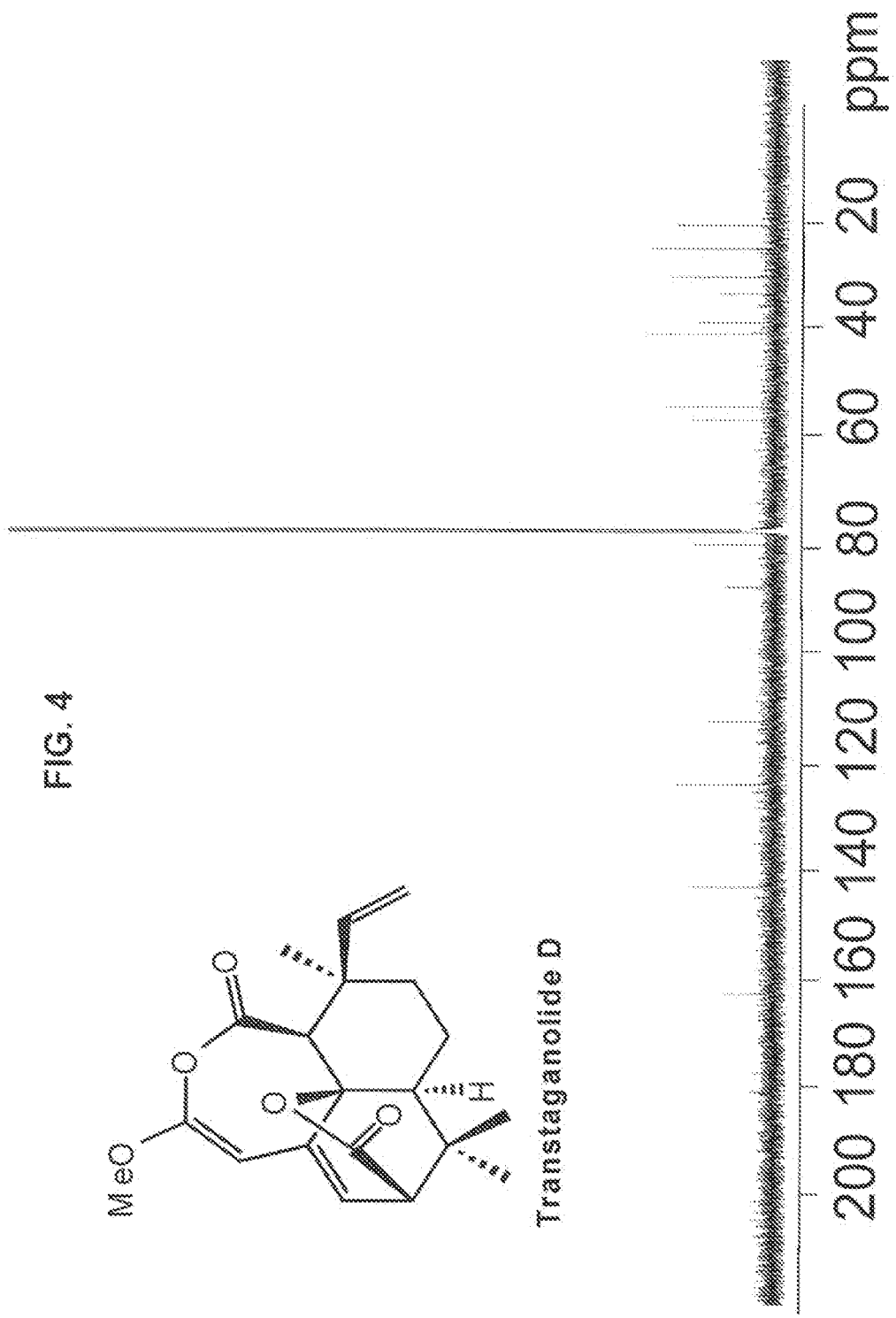
FIG. 4 is a $^{13}$C NMR spectrum of transtaganolide D (1b), according to aspects of the present invention.

FIG. 4 shows a $^{13}$C NMR spectrum of Transtaganolide D (1b). $^{13}$C NMR (125 MHz, CDCl$_3$) δ 171.7, 162.6, 156.7, 142.9, 137.7, 123.9, 112.1, 87.3, 79.4, 56.3, 54.0, 53.3, 48.4, 40.5, 38.4, 33.3, 29.9, 28.5, 24.8, 20.5.

FTIR (Neat Film NaCl) 2964, 2929, 2872, 1764, 1760, 1738, 1667, 1620, 1467, 1334, 1267, 1235, 1195, 1177, 1106, 1009, 954, 827 cm$^{-1}$. HRMS (Multimode-ESI/APCI) m/z calc'd for C$_{20}$H$_{24}$O$_5$ [M+H]$^+$: 345.1697, found 345.1698; MP: 135-160° C. (at these temperatures decarboxylation is thought to occur, as the crystalline sample and the resulting liquid were vigorously bubbling throughout the measurement; thus it is unclear whether thermal decomposition precluded state change) (Appendix).

Example 4

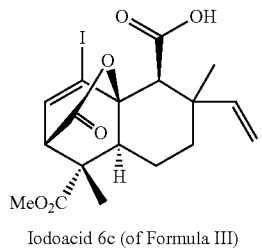 [SMILES: C=CC1(C)CC[C@H]2[C@](C)(C(=O)OC)[C@@H]3C=C(I)[C@]2(OC3=O)[C@H]1C(=O)O]

Ester 7b

Ester 7b. To a solution of geraniol derivative 12 (140 mg, 0.70 mmol, 1.0 equiv) and iodopyrone acid 13 (210 mg, 0,70 mmol, 1.0 equiv) in acetonitrile (7.0 ml) was added N,N'-dicyclohexylcarbodiimide (190 mg, 0.91 mmol, 1.3 equiv) at 0° C. The reaction was warmed to 25° C. and stirred for seven additional hours. The reaction mixture was then filtered through a pad of Celite, and then concentrated by rotary evaporation. The crude reaction mixture was then chromatographed (ethyl acetate in hexane 0⇒30% on SiO$_2$) to give 300 mg (94%) of 7b as a pale yellow oil.

Figure 9:
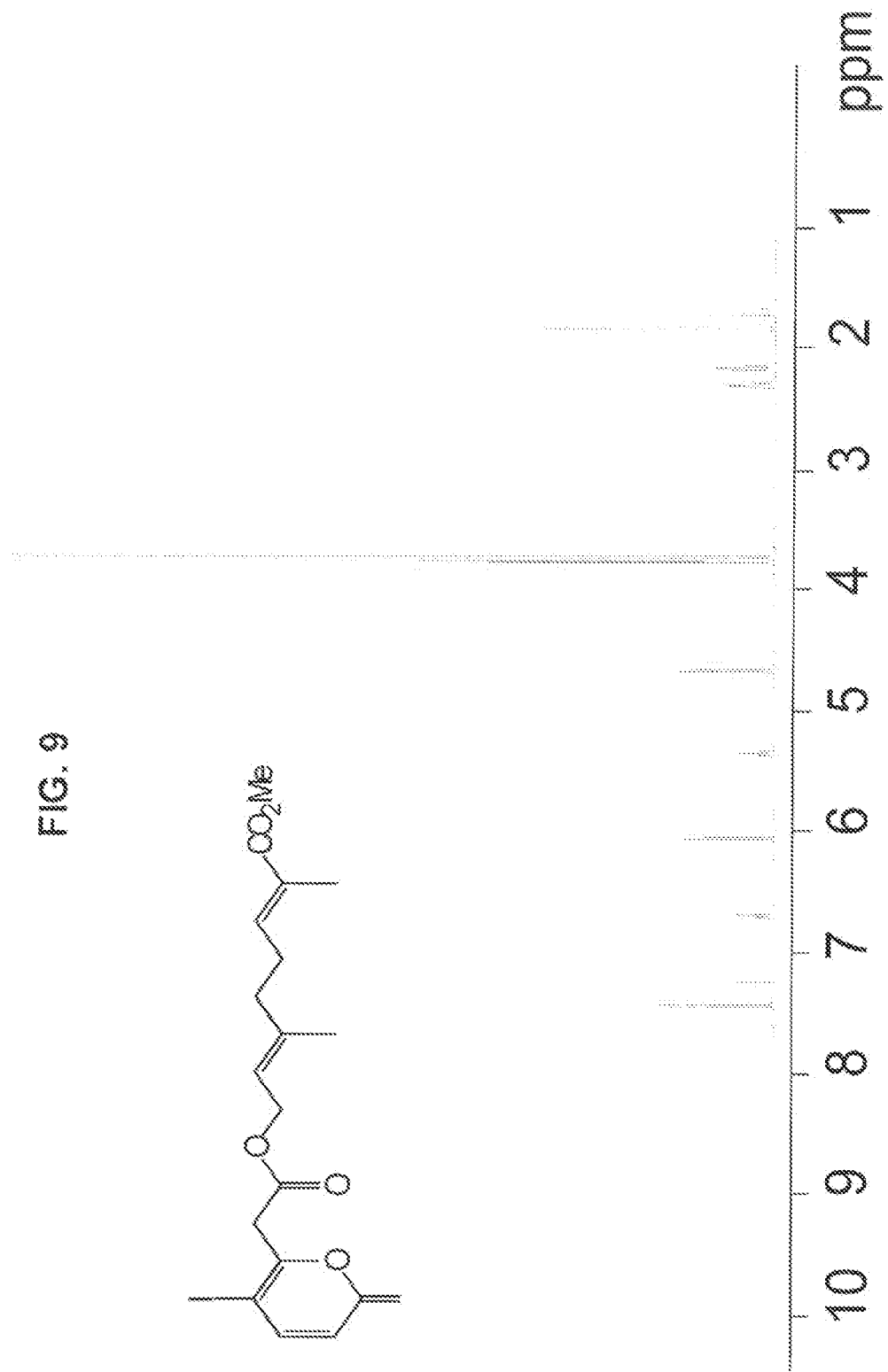
FIG. 9 is a $^1$H NMR spectrum of ester (7b), according to aspects of the present invention.

FIG. 9 shows a $^1$H NMR spectrum of ester 7b. $^1$H NMR (500 MHz, CDCl$_3$) δ 7.45 (d, J=10.0 Hz, 1H), 6.70 (tq, J=1.5, 7.5 Hz, 1H), 6.06 (d, J=10.0 Hz, 1H), 5.35 (tq, J=1.5, 7.0 Hz, 1H), 4.67 (d, J=7.0 Hz, 2H), 3.77 (s, 2H), 3.72 (s, 3H), 2.30 (q, J=7.5 Hz, 2H), 2.16 (t, J=7.5 Hz, 2H), 1.83 (q, J=1.5 Hz, 3H), 1.72 (q, J=1.5 Hz, 3H).

$^{13}$C NMR (125 MHz, CDCl$_3$) δ 168.5, 166.6, 160.3, 157.9, 151.2, 142.0, 141.3, 128.0, 118.3, 116.1, 70.6, 62.5, 51.7, 42.6, 38.0, 26.8, 16.5, 12.4.

FTIR (Neat Film NaCl) 2988, 2950, 1738, 1714, 1438, 1366, 1268, 1232, 1126, 1082, 1023, 955, 745 cm$^{-1}$. HRMS (Multimode-ESI/APCI) m/z calc'd for C$_{18}$H$_{25}$NO$_6$I [M+NH$_4$]$^+$: 478.0725 (Appendix).

Example 5

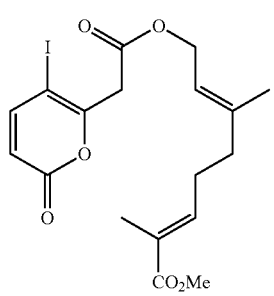

Iodoacid 6c (of Formula III)

Iodoacid 6c. To a solution of 7b (96 mg, 0.21 mmol, 1.0 equiv) in toluene (1.1 mL) in a sealed tube were successively added triethylamine (6.0 μL, 0.042 mmol, 0.20 equiv) and N,O-bis(trimethylsilyl)acetamide (100 μL, 0.42 mmol, 2.0 equiv). The reaction mixture was heated to 110° C. and stirred for 20 minutes, then cooled to 25° C. The reaction mixture was diluted with toluene (250 ml) and heated to 100° C. for 48 hours. The reaction was then cooled to 25° C., the solvent removed by rotary evaporation, and the crude residue chromatographed (hexane/ethyl acetate/acetic acid, 1:1:0.01 on SiO$_2$) to give 64 mg (67%) of 6c as a colorless foam.

Figure 10:
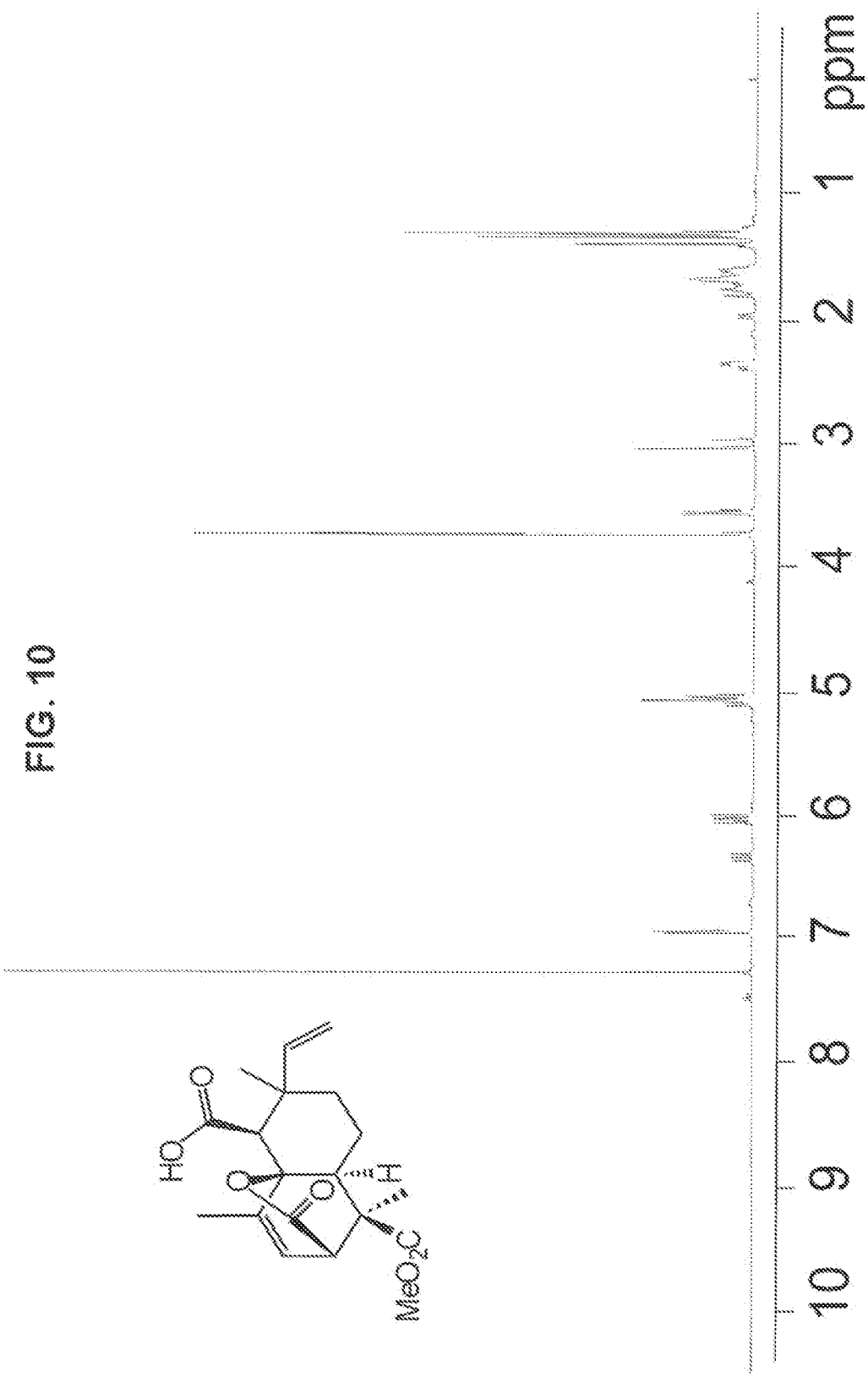
FIG. 10 is a $^1$H NMR spectrum of iodoacid (6c), according to aspects of the present invention.

FIG. 10 shows a $^1$H NMR spectrum of iodoacid 6c. Major: $^1$H NMR (500 MHz, CDCl$_3$) δ 6.93 (d, J=6.5 Hz, 1H), 6.02 (dd, J=10.5, 17.5 Hz, 1H), 5.07-5.03 (m, 2H), 3.72 (s, 3H), 3.56-3.53 (m, 1H), 3.03 (s, 1H), 2.40-2.33 (m, 1H), 1.77-1.56 (m, 4H), 1.32 (s, 3H), 1.30 (s, 3H). FIG. 11 shows a $^{13}$C NMR spectrum of iodoacid 6c. $^{13}$C NMR (125 MHz, CDCl$_3$) δ 174.8, 169.2, 169.1, 147.9, 139.7, 111.6, 99.2, 84.2, 59.2, 53.0, 52.6, 47.8, 44.5, 40.0, 38.1, 20.8, 18.4.

Minor: $^1$H NMR (500 MHz, CDCl$_3$) δ 6.93 (d, J=6.5 Hz, 1H), 6.33 (dd, J=11.0, 17.5 Hz, 1H), 5.10 (d, J=11.0 Hz, 1H), 5.07-5.03 (m, 1H), 3.72 (s, 3H), 3.56-3.53 (m, 1H), 2.97 (s, 1H), 2.40-2.33 (m, 1H), 1.98-1.95 (m, 1H), 1.77-1.56 (m, 3H), 1.30 (s, 3H); $^{13}$C NMR (125 MHz, CDCl$_3$) δ 174.8, 169.1, 169.0, 140.4, 140.0, 113.5, 98.8, 84.3, 60.6, 52.7, 48.0, 39.45, 38.5, 29.8, 20.8, 20.8, 20.8.

FTIR (Neat Film NaCl) 3080, 2951, 1756, 1739, 1734, 1700, 1559, 1506, 1457, 1211, 911, 756 cm$^{-1}$; HRMS (Multimode-ESI/APCI) m/z calc'd for $C_{18}H_{22}O_6I$ [M+H]$^+$: 461.0456, found 461.0460 (Appendix).

Example 6

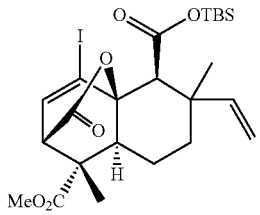

tert-butyldimethylsilyl ester 6d (of Formula III)

tert-Butyldimethylsilyl ester 6d. To a solution of 6c (89 mg, 0.11 mmol, 1.0 equiv) in dimethylformamide (0.52 mL) were added tert-butyldimethylsilylchloride (150 mg, 0.97 mmol, 5.0 equiv) and imidazole (130 mg, 1.9 mmol, 10 equiv). The reaction mixture was warmed to 40° C. and stirred for 3 hours. The crude mixture was then diluted with saturated aqueous NaCl (1 mL) and extracted with diethyl ether/hexane (1:1) (3×2 mL). The combined organic extracts were washed with saturated aqueous NaCl (3×1 mL), dried over $Na_2SO_4$, and concentrated by rotary evaporation to yield 76 mg (68%) of 6d as a pale yellow powder.

Procedure 2. To a solution of 6c (61 mg, 0.13 mmol, 1 equiv) in acetonitrile (0.13 mL, 1.0 M) was added N-methyl-N-(tert-butyldimethylsilyl)trifluoroacetamide (320 mg, 1.3 mmol, 10 equiv) at 25° C. and stirred for 15 minutes. The reaction mixture was diluted with saturated aqueous NaCl (1 mL) and extracted with diethyl ether/hexane (1:1) (3×2 mL). The combined organic extracts were washed with saturated aqueous $KHSO_4$ (1 mL) and then with saturated aqueous NaCl (3×1 mL). The combined organics were dried over $Na_2SO_4$, and concentrated by rotary evaporator. The crude oil was chromatographed (ethyl acetate in hexane 10⇒50% on $SiO_2$) to yield 51 mg (66%) of 6d as a white powder.

Figure 12:
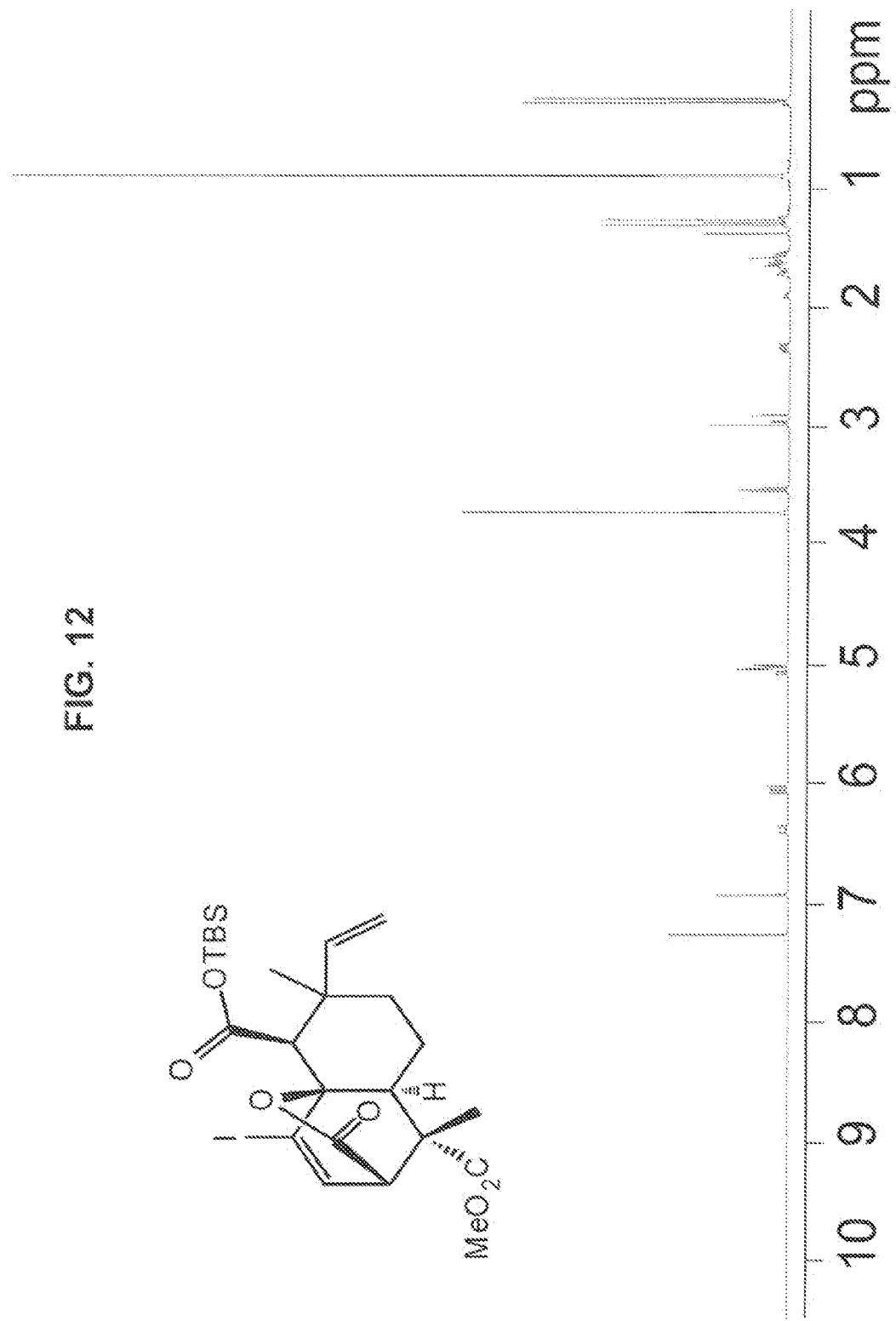
FIG. 12 is a $^1$H NMR spectrum of tert-butyldimethylsilyl ester (6d), according to aspects of the present invention.
Figure 13:
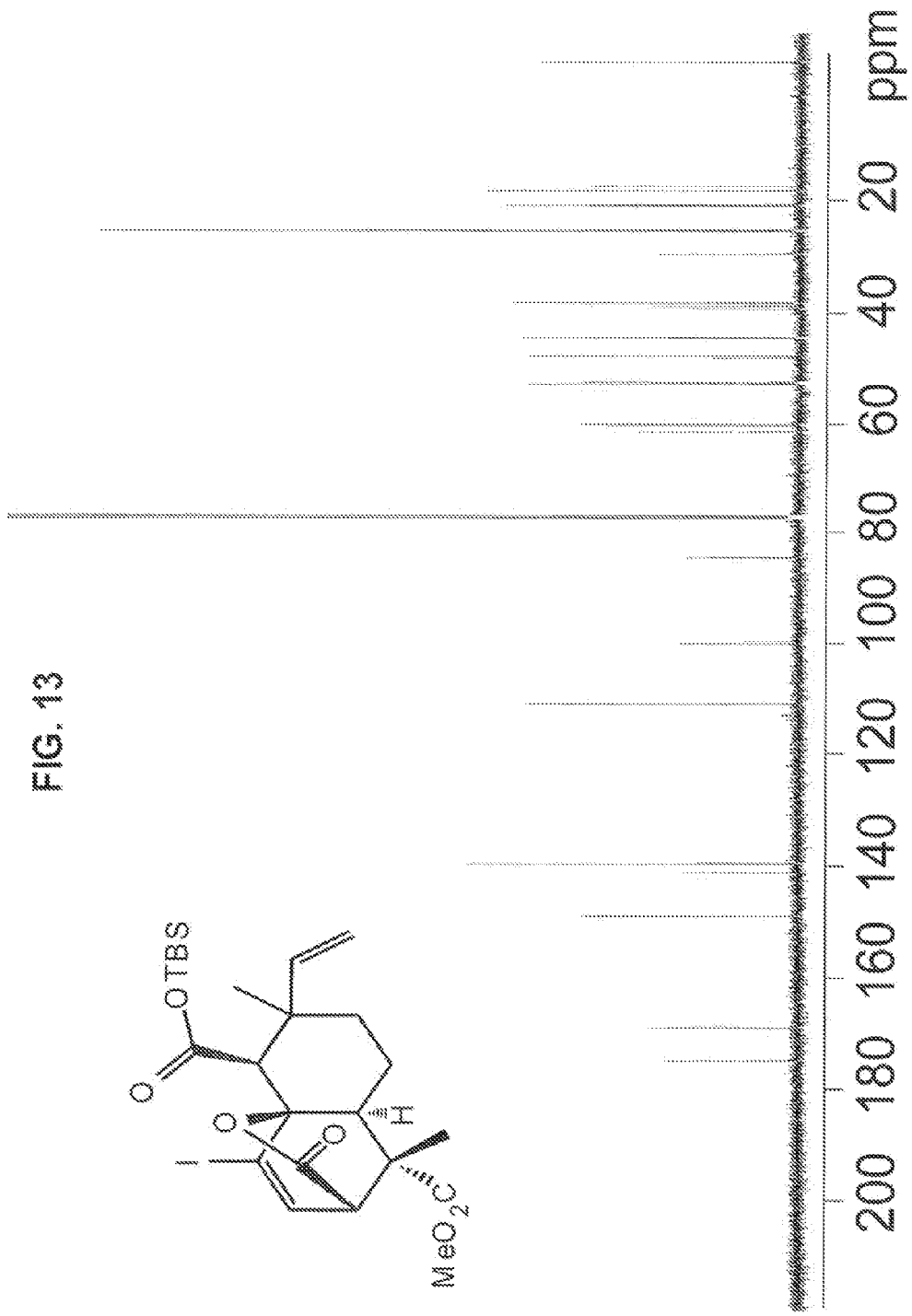
FIG. 13 is a $^{13}$C NMR spectrum of tert-butyldimethylsilyl ester (6d), according to aspects of the present invention.

FIG. 12 shows a $^1$H NMR spectrum of tert-Butyldimethylsilyl ester 6d. Major: $^1$H NMR (500 MHz, CDCl$_3$) δ 6.92 (d, J=6.5 Hz, 1H), 6.04 (dd, J=10.5, 17.5 Hz, 1H), 5.01 (d, J=10.5 Hz, 1H), 5.01 (d, J=17.5 Hz, 1H), 3.72 (s, 3H), 3.53 (d, J=6.5 Hz, 1H), 2.98 (s, 1H), 2.38-2.31 (m, 1H), 1.76-1.54 (m, 4H), 1.31 (s, 3H), 1.37 (s, 3H), 0.90 (s, 9H), 0.29 (s, 3H), 0.26 (s, 3H). FIG. 13 shows a $^{13}$C NMR spectrum of tert-Butyldimethylsilyl ester 6d. $^{13}$C NMR (125 MHz, CDCl$_3$) δ 174.9, 169.1, 168.9, 1489, 139.4, 110.7, 99.9, 84.2, 60.4, 53.0, 52.7, 48.0, 44.7, 40.2, 38.5, 25.5, 20.9, 18.2, 17.5, −4.80, −4.80.

Minor: $^1$H NMR (500 MHz, CDCl$_3$) δ 6.92 (d, J=6.5 Hz, 1H), 6.37 (dd, J=11.0, 17.5 Hz, 1H), 5.06 (d, J=11.0 Hz, 1H), 5.03-4.99 (m, 1H), 3.72 (s, 3H), 3.51 (d, J=6.5 Hz, 1H), 2.90 (s, 1H), 2.38-2.31 (m, 1H), 1.92-1.88 (m, 1H), 1.76-1.54 (m, 3H), 1.38 (s, 3H), 1.29 (s, 3H), 0.89 (s, 9H), 0.29 (s, 3H), 0.28 (s, 3H). $^{13}$C NMR (125 MHz, CDCl$_3$) δ 174.9, 169.1, 169.1, 168.9, 141.0, 139.7, 113.0, 99.5, 84.3, 61.8, 52.9, 48.3, 39.6, 39.0, 29.7, 25.3, 20.9, 20.8, 17.5, −4.90, −4.90.

IR (Neat Film NaCl) 2951, 2928, 2856, 1767, 1733, 1717, 1447, 1274, 1251, 1215, 1191, 968, 843, 828, 792, 736 cm$^{-1}$; HRMS (Multimode-ESI/APCI) m/z calc'd for $C_{24}H_{36}O_6ISi$ [M+H]$^+$: 575.1320, found 575.1317 (Appendix).

Example 7

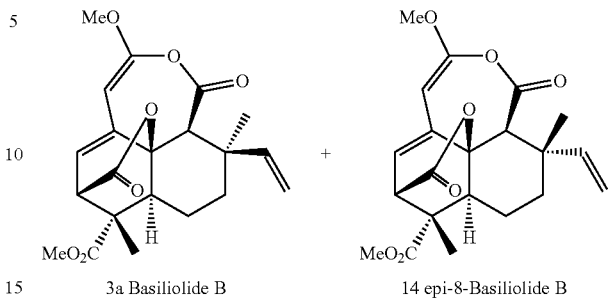

3a Basiliolide B      14 epi-8-Basiliolide B

Basiliolides (3a, 14). In a nitrogen filled glovebox, to a solution of 6d (15 mg, 0.030 mmol, 1.0 equiv) and Pd(PPh$_3$)$_4$ (35 mg, 0.030 mmol, 1.0 equiv) in dimethylformamide (0.30 mL, 0.10 M) was added tributyl(2-methoxyethynyl)stananne (10) (53 mg, 0.050 mmol, 5.0 equiv). The reaction was stirred at 30° C. for 16 hours, then treated with water (30 µL) and stirred at 25° C. for an additional 1 hour. The mixture was then diluted with ethyl acetate (1 mL) and washed with water (4×0.5 mL) and concentrated by rotary evaporation. The crude oil was purified by normal phase HPLC to yield 0.6 mg (6%) of basiliolide B (3a) and 1.2 mg (12%) of epi-8-basiliolide B (14) as white powders.

Procedure 2. In a nitrogen filled glovebox, to a solution of 6b (16 mg, 0.030 mmol, 1.0 equiv) and Pd(t-Bu$_3$P)$_2$ (15 mg, 0.030 mmol, 1.0 equiv) in dimethylformamide (0.30 mL, 0.10 M) was added tributyl(2-methoxyethynyl)stananne (43 mg, 0.12 mmol, 4.0 equiv). The reaction was stirred at 30° C. for 10 hours, and then an addition aliquot (22 mg, 0.060 mmol, 2.0 equiv) of stannane 10 was added and stirred for an additional two hours. The reaction was treated with water (30 µL) and stirred at 25° C. for an additional 1 hour. The crude reaction mixture was diluted with ethyl acetate (1 mL) and washed with water (4×0.5 mL) and concentrated by rotary evaporation. The crude oil was purified by normal phase HPLC to yield 0.6 mg (5%) of basiliolide B (3a) and 1.6 mg (14%) of epi-8-basiliolide B (14) as white powders.

Figure 5:
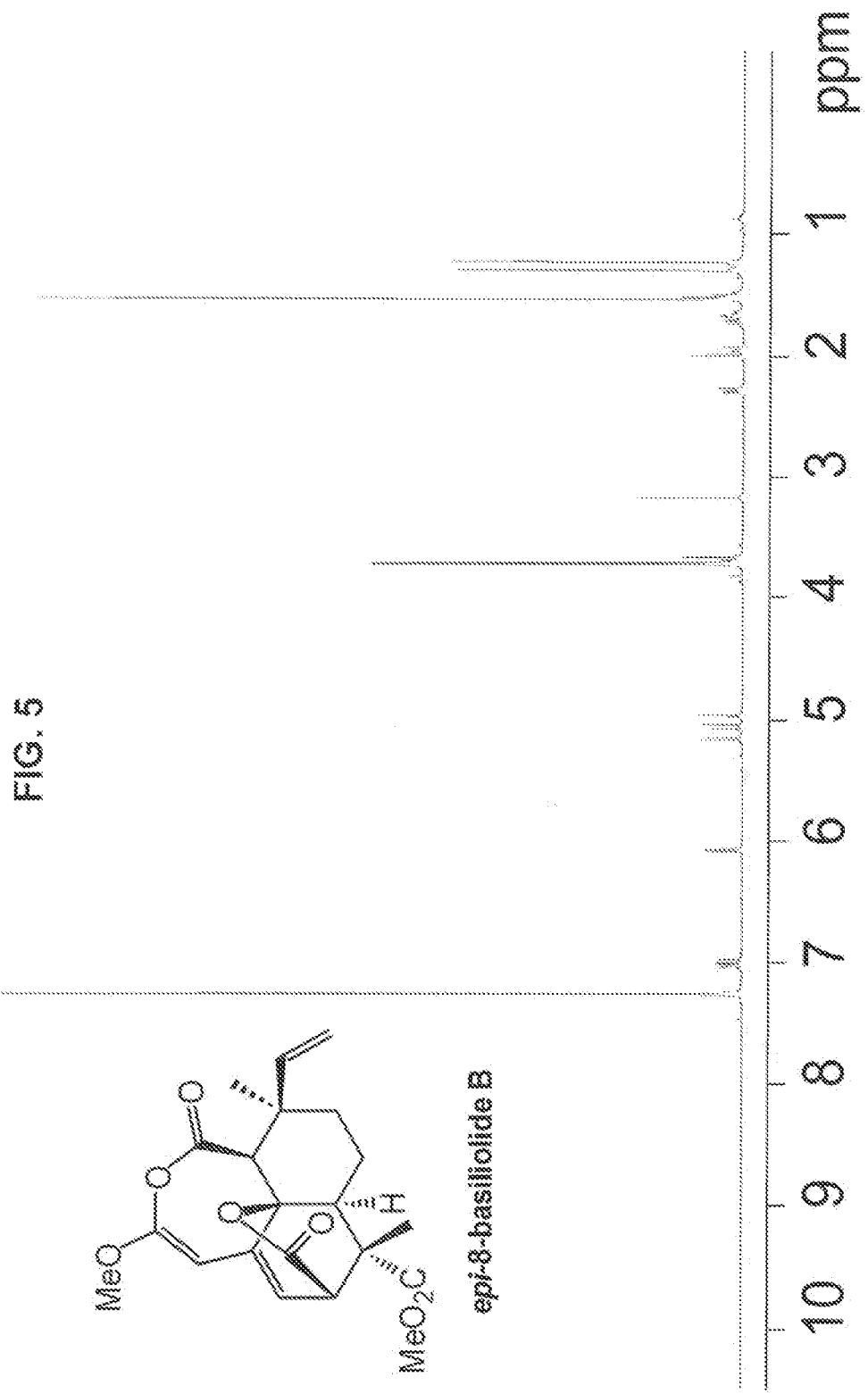
FIG. 5 is a $^1$H NMR spectrum of basiliolide B (3a), according to aspects of the present invention.

FIG. 5 shows a $^1$H NMR spectrum of Basiliolide B (3a). $^1$H NMR (500 MHz, CDCl$_3$) δ 7.00 (dd, J=11.5, 18 Hz, 1H), 6.08 (d, J=5.5 Hz, 1H), 5.17 (d, J=11.5 Hz, 1H), 5.06 (d, J=18 Hz, 1H), 4.96 (s, 1H), 3.72 (s, 3H), 3.71 (s, 3H), 3.67 (d, J=5.5 Hz, 1H), 3.17 (s, 1H), 2.29 (dd, J=5.0 Hz, 1H), 1.96 (dt, J=3.0 Hz, 13.5 Hz, 1H), 1.74-1.65 (m, 2H), 1.54-1.48 (m, 1H), 1.30 (s, 3H), 1.24 (s, 3H). FIG. 6 shows a $^{13}$C NMR spectrum of Basiliolide B (3a). $^{13}$C NMR (125 MHz, CDCl$_3$) δ 175.2, 170.1, 162.3, 156.7, 142.7, 139.2, 123.4, 112.3, 87.0, 79.2, 56.4, 53.3, 52.9, 50.0, 44.8, 44.7, 40.2, 38.5, 28.6, 21.0, 20.8.

FTIR (Neat Film NaCl) 2951, 2875, 1791, 1761, 1771, 1767, 1733, 1668, 1663, 1456, 1334, 1262, 1230, 1213, 1180, 1107, 1011, 960, 908, 833, 736 cm$^{-1}$. HRMS (Multimode-ESI/APCI) m/z calc'd for $C_{21}H_{24}O_7$ [M+H]$^+$: 389.1595, found 389.1599 (Appendix).

$^1$H NMR (500 MHz, CDCl$_3$) δ 6.06 (d, J=6.0 Hz, 1H), 5.80 (dd, J=10.5, 17.5 Hz, 1H), 5.09 (d, J=10.5 Hz, 1H), 5.05 (d, J=17.5 Hz, 1H), 4.94 (s, 1H), 3.71 (s, 3H), 3.70 (s, 3H), 3.66 (d, J=6.0 Hz, 1H), 3.26 (s, 1H), 2.25 (dd, J=7.0, 12.0 Hz, 1H), 1.79-1.67 (m, 4H), 1.61 (s, 3H), 1.34 (s, 3H). $^{13}$C NMR (125

MHz, CDCl₃) δ 175.1, 170.1, 162.0, 146.2, 139.5, 123.2, 113.0, 87.0, 79.0, 56.3, 52.9, 50.5, 49.9, 44.7, 44.6, 38.5, 38.2, 21.0, 20.3, 19.3.

FTIR (Neat Film NaCl) 2980, 2951, 2929, 1770, 1767, 1761, 1732, 1668, 1619, 1442, 1335, 1261, 1219, 1182, 1106, 971, 960, 918, 834, 732 cm$^{-1}$. HRMS (Multimode-ESI/APCI) m/z calc'd for $C_{21}H_{24}O_7$ [M+H]$^+$: 389.1595, found 389.1604 (Appendix).

Example 8

Tributyl(2-methoxyethynyl)stannane (10) (of Formula II)

Tributyl(2-methoxyethynyl)stannane (10). To a solution of freshly distilled diethylamine (9.6 mL, 92 mmol, 3.9 equiv) in tetrahydrofuran (300 mL) at 0° C. was added n-butyllithium (2.5 M in hexanes, 32 mL, 80 mmol, 3.4 equiv). After stirring for 10 min, 1,1-dimethoxy-2-chloro-acetaldehyde (4.0 mL, 26 mmol, 1.1 equiv) was added dropwise to the reaction mixture. The reaction was stirred for 2 hours at 0° C. Tributyltin chloride (6.2 mL, 24 mmol, 1.0 equiv) was then added to the reaction mixture. The reaction was warmed to 23° C. over 1 hour and stirred for 8 hours. The volatiles were removed in vacuo and the reaction mixture was re-suspended in hexane (30 mL) and filtered through a glass frit under an argon atmosphere. The solution was then re-concentrated by rotary evaporation and distilled by Kugelrohr to yield 6.4 g (78%) of 10 as a colorless oil.

$^1$H NMR (500 MHz, CDCl₃) δ 3.87 (s, 3H), 1.54 (m, 6H), 1.33 (sextet, J=7.5 Hz, 6H), 0.94 (m, 6H), 0.90 (t, J=7.5 Hz, 9H).). $^{13}$C NMR (125 MHz, CDCl₃) δ 114.7, 65.8, 31.5, 28.9, 27.0, 13.7, 11.2.

FTIR (Neat Film NaCl) 2955, 2927, 2871, 2161, 1457, 1208, 1126, 910, 865 cm$^{-1}$; Elemental analysis found: C, 52.40%; H, 8.54%. Calculated for $C_{15}H_{30}OSn$: C, 52.20%; H, 8.76% (Appendix).

Example 9

Zn acetaldehyde (of Formula II)

Zn acetaldehyde was made using Negishi cross-coupling. In a nitrogen filled glove box, a flask was charged with THF (1.15 mL) and diethylamine (0.40 mL). The reaction mixture was cooled to 0_C and n-BuLi (0.34 mL of 10M solution in hexanes) was slowly added. After stirring for 2 hours, chlorodimethoxyacetaldehyde (1 mmol 0.114 mL) was added slowly. Subsequent to stirring for 2 hours, the reaction mixture was transferred to a flask charged with anhydrous $ZnCl_2$ (150 mg) and stirred at 0° C. for an additional 20 minutes. Concurrently, a flame dried microwave vial was charged with $Pd_2(dba)_3$ (0.9 mg, 0.05 equiv.), Xantphos (20 uL, 0.10 equiv), THF (0.50 mL), and iodoacid (1 equiv). After stirring for 2 hours, the crude Zn acetaldehyde (0.03 mL) was added via syringe into the microwave vial, and the reaction mixture sealed. Using microwaves, the reaction was heated to 100° C. for 2 minutes. After cooling of the reaction mixture, the reaction was passed through a short pad of silica, diluted with acetonitrile. 100 uL of pH 7 phosphate buffer was added and the reaction was stirred for 30 minutes at room temperature. Following normal phase HPLC, transtaganolides C and D were isolated in 21% and 10% yield. The synthetic transtaganolides are spectroscopically indistinguishable from the natural isolates.

Example 10

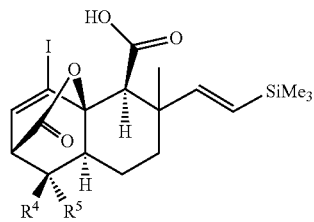

Trimethylsilyl iodoacid (of Formula III)

Trimethylsilyl iodoacid. 1-trimethylsilyl geraniol (1 mmol, 1 equiv) was added to a solution if iodoacid (1 mmol, 1 equiv) in acetonitrile (10 mL) at 0° C. DCC (1.1 mmol, 1.1 equiv) was added and the reaction was stirred for 1 hour. The reaction mixture was then dilated with ethyl acetate and washed with 1% HCl (aq.) (3×100 mL). The organic layer was dried with $MgSO_4$, and solvent was removed by rotary evaporation. The resulting amber syrup was chromatographed on SiO2, using 25% ethyl acetate in hexanes as an eluent, to produce the pyrone ester in 96% yield. A $^1$H NMR spectrum of this $SIM_{E3}$ pyrone ester is shown in FIG. 14. The enantiomeric excess was determined by chiral SFC (super critical fluid chromatography) and comparison to a racemic sample. SFC is disclosed in C. White *J. Chromatogr. A* 2005, 1074, 163-173.

The Ireland-Claisen/Diels-Alder cyclization is the same for $SiMe_3$ pyrone ester as for ester 7b, as disclosed herein (Scheme 4, Example 4, with reference to Larock, *J. Org. Chem.* 2003, 68, 5936-5942; Li, *Synthesis,* 2007, 3, 400-406; H. M. Nelson et al., 2009, supra; and Johansson et al., 2009), to produce the iodoacid-SiMe₃. The $^1$H NMR spectrum is shown in FIG. 15.

Removal of the $SiMe_3$. Trimethylsilyl-iodoacid (25 mg) was dissolved in acetonitrile (1 mL) and $HBF_4$ (aq.) (0.05 mL) was added. The reaction mixture was stirred for 3 hours at 25° C. The reaction mixture was then diluted with ethyl acetete and washed with 1% HCl (aq.) 3×1 mL). The organic layer was dried with $MgSO_4$, and solvent was removed by rotary evaporation. The resulting amber syrup was chromatographed on $SiO_2$, using 25% ethyl acetate in hexanes as an eluent, to produce the iodoacid in 96% yield. The compound was spectroscopically identical to the previously prepared racemic compound.

As disclosed throughout and evidenced by the NMR spectra of FIGS. 1-6, synthetic compounds of Formula I are provided. Additionally methods of synthesizing compounds of Formula I are provided including reacting compounds of Formula II and Formula III. Furthermore, methods are provided for using silyl compounds for synthesizing enantiomeric enrichment of a compound of Formula I. Accordingly, synthetic compounds and the method of synthesis of the present invention, provide increased quantities and enrichment of desired compounds of Formula I, such as basiliolides and transtaganolides.

While the present invention has been illustrated and described with reference to certain exemplary embodiments, those of ordinary skill in the art will understand that various modifications and changes may be made to the described embodiments without departing from the spirit and scope of the present invention, as defined in the following claims.

What is claimed is:

1. A compound having a structure represented by Formula IV:

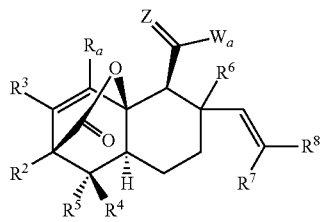

Formula IV wherein:
$R_a$ is selected from:
alkenyl substituted with alkoxy, thioalkoxy, alkylamino, or dialkylamino, and
alkynyl substituted with alkoxy, thioalkoxy, alkylamino, or dialkylamino;
$W_a$ is —$OR^x$ wherein $R^x$ is selected from hydrogen, hydrocarbyl, and silyl group;
$R^2$ and $R^3$ are each hydrogen;
$R^4$ and $R^5$ are each independently selected from hydrogen, hydrocarbyl, silyl, and —C(O)O(hydrocarbyl);
$R^6$ is hydrogen or hydrocarbyl;
$R^7$ and $R^8$ are each independently selected from hydrogen, hydrocarbyl, and silyl; and
Z is O.

2. The compound of claim 1, wherein $R_a$ is alkenyl substituted with alkoxy or alkynyl substituted with alkoxy.

3. The compound of claim 1, wherein $W_a$ is —$OR^x$ in which $R^x$ is a silyl group.

4. The compound of claim 3, wherein the silyl group is a tert-butyl dimethyl silyl group or a trimethyl silyl group.

5. The compound of claim 2, wherein $W_a$ is —$OR^x$ in which $R^x$ is a silyl group.

6. The compound of claim 5, wherein the silyl group is a tert-butyl dimethyl silyl group or a trimethyl silyl group.

* * * * *